(12) United States Patent
Sreenivasan et al.

(10) Patent No.: US 10,561,962 B2
(45) Date of Patent: Feb. 18, 2020

(54) DYNAMIC MELT CRYSTALLIZATION PROCESS FOR PURIFYING DICYCLOPENTADIENE FROM A MIXED LIQUID HYDROCARBON STREAM

(71) Applicant: SABIC GLOBAL TECHNOLOGIES B.V., Bergen op Zoom (NL)

(72) Inventors: P. S. Sreenivasan, Bengaluru (IN); Omkar D. Gadgil, Bengaluru (IN); P. S. Mahabala, Bengaluru (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 16/069,274

(22) PCT Filed: Dec. 29, 2016

(86) PCT No.: PCT/IB2016/001951
§ 371 (c)(1),
(2) Date: Jul. 11, 2018

(87) PCT Pub. No.: WO2017/122040
PCT Pub. Date: Jul. 20, 2017

(65) Prior Publication Data
US 2019/0022553 A1    Jan. 24, 2019

Related U.S. Application Data

(60) Provisional application No. 62/277,641, filed on Jan. 12, 2016.

(51) Int. Cl.
*B01D 9/00* (2006.01)
*C07C 7/14* (2006.01)
*C07C 13/61* (2006.01)

(52) U.S. Cl.
CPC ............ *B01D 9/0013* (2013.01); *B01D 9/004* (2013.01); *C07C 7/14* (2013.01); *C07C 13/61* (2013.01);
(Continued)

(58) Field of Classification Search
CPC .. C07C 7/14; C07C 13/61; C07C 2/50; C07C 7/005; C07C 51/43; C07C 15/08;
(Continued)

(56) References Cited

U.S. PATENT DOCUMENTS 2,354,895 A * 8/1944 Ward .................. C07C 2/50
585/362
2,540,977 A    2/1951 Arnold
(Continued)

FOREIGN PATENT DOCUMENTS

DE    1931959 A1    1/1970
EP    0726306 A1    8/1996
(Continued)

OTHER PUBLICATIONS

Filing receipt and specification for provisional application entitled "A Dynamic Melt Crystallization Process for Purifying Dicyclopentadiene from a Mixed Liquid Hydrocarbon Stream," by P. S. Sreenivasan, et al., filed Jan. 12, 2016 as U.S. Appl. No. 62/277,641.
(Continued)

*Primary Examiner* — Sharon Pregler
(74) *Attorney, Agent, or Firm* — Norton Rose Fulbright US LLP

(57) ABSTRACT

A dynamic process for purifying dicyclopentadiene from a mixed liquid hydrocarbon stream comprising dicyclopentadiene and one or more of a $C_5$ paraffin, a $C_5$ olefin, co-dimers, cyclopentadiene, benzene, vinyl norbornene, bicyclononadiene, propenyl norbornene, isopropenyl
(Continued)

norbornene, methylbicyclononadiene, methyldicyclopentadiene, and various minor organic impurities is introduced, wherein the dicyclopentadiene is separated from the mixed liquid hydrocarbon stream by melt crystallizing sweating and collecting dicyclopentadiene.

15 Claims, 19 Drawing Sheets

(52) U.S. Cl.
CPC .. *B01D 2009/0086* (2013.01); *C07C 2603/68* (2017.05)

(58) Field of Classification Search
CPC ..... C07C 57/04; C07C 15/24; C07C 2603/68; B01D 9/0013; B01D 9/004; B01D 9/0059; B01D 9/0072; B01D 9/0036
See application file for complete search history.

(56) References Cited

U.S. PATENT DOCUMENTS

| | | | | |
|---|---|---|---|---|
| 2,622,114 | A | * | 12/1952 | Carney ................ B01D 9/0013 554/211 |
| 3,597,164 | A | * | 8/1971 | Proabd ................ B01D 9/0013 422/245.1 |
| 4,085,776 | A | | 4/1978 | Derrick, Jr. |
| 4,560,108 | A | | 12/1985 | Rubinstein |
| RE32,241 | E | * | 9/1986 | Saxer ................... B01D 9/0013 62/542 |
| 5,504,247 | A | | 4/1996 | Saxer et al. |

FOREIGN PATENT DOCUMENTS

| | | |
|---|---|---|
| GB | 557339 | 11/1943 |
| GB | 1066032 | 4/1967 |
| GB | 1316748 | 5/1973 |
| WO | 2017122040 A1 | 7/2017 |

OTHER PUBLICATIONS

Foreign communication from the priority International Application No. PCT/IB2016/001951, International Search Report and Written Opinion, dated Apr. 20, 2017, 13 pages.
Foreign communication from the priority International Application No. PCT/IB2016/001951, International Preliminary Report on Patentability of the International Preliminary Examining Authority, dated Jul. 26, 2018, 8 pages.
"Fractional Crystallization," Sulzer Chemtech, 16 pages.
Tully, William F., "A Capillary Column For the Gas Chromatographic Analysis of Dicyclopentadiene," Journal of Chromatographic Science, Oct. 1971, pp. 635-638, vol. 9.

* cited by examiner

DYNAMIC MELT CRYSTALLIZATION PROCESS FOR PURIFYING DICYCLOPENTADIENE FROM A MIXED LIQUID HYDROCARBON STREAM

CROSS REFERENCE TO RELATED APPLICATIONS

This application is a filing under 35 U.S.C. 371 of International Application No. PCT/IB2016/001951 filed Dec. 29, 2016, entitled "A Dynamic Melt Crystallization Process for Purifying Dicyclopentadiene from a Mixed Liquid Hydrocarbon Stream," which claims the benefit of U.S. Provisional Application No. 62/277,641 filed Jan. 12, 2016, entitled "A Dynamic Melt Crystallization Process for Purifying Dicyclopentadiene from a Mixed Liquid Hydrocarbon Stream," which applications are incorporated by reference herein in their entirety.

BACKGROUND OF THE INVENTION

Technical Field

The present invention relates to a dynamic process of purifying dicyclopentadiene from a mixed liquid hydrocarbon stream by melt crystallizing, sweating, and collecting dicyclopentadiene.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dicyclopentadiene is a waxy, colorless, flammable liquid coproduced in large quantities by steam cracking or from pyrolysis of naphtha and other petroleum fractions to form ethylene and propylene. Dicyclopentadiene is a mixture of two optical isomers endo-dicyclopentadiene and exo-dicyclopentadiene, with the major component being endo-dicyclopentadiene. At room temperature, dicyclopentadiene is a colorless solid crystal with a camphor-like odor, and its melting point is approximately 33.6° C. Dicyclopentadiene has been an extremely useful chemical compound for many decades. As a monomer it is used in preparation of a wide variety of resins such as unsaturated polyesters, epoxies, aromatic hydrocarbons and phenolic resins, Cyclic Olefin Copolymers (COCs), flavors and fragrances, alkyds, acrylates, poly-dicyclopentadiene and so forth. Dicyclopentadiene is also used in production of paints, varnishes, insecticides, elastomers, flame retardants for plastics, and hot melt adhesives.

The required purity of dicyclopentadiene for manufacturing unsaturated polyester resins is in the range of 84-90% dicyclopentadiene by weight. The required purity of dicyclopentadiene for manufacturing Cyclic Olefin Copolymers, flavors, and fragrances is in the range 90-94% dicyclopentadiene by weight, while this value is greater than 98% dicyclopentadiene by weight for poly-dicyclopentadiene.

One important application of dicyclopentadiene is toward manufacturing poly-dicyclopentadiene. Demand for poly-dicyclopentadiene has increased significantly in the past few years in applications such as fascia panels for automobiles, sanitary-ware, house-hold appliances etc., where poly-dicyclopentadiene has advantages of superior aesthetics and lower cost over competing products. Therefore there has been increasing interest in exploring more sustainable and cost effective ways of manufacturing dicyclopentadiene of higher purity.

Conventional processes of separation and purification of dicyclopentadiene involves repetitive cracking a stream of hydrocarbon mixture, distilling cyclopentadiene at an overhead of a distillation column, and subsequently dimerizing cyclopentadiene compounds under controlled reaction conditions to form dicyclopentadiene. These processes are performing at a relatively high temperature range of around 150° C. to 250° C. and thus are very energy intensive. Additionally, in these operations separation is achieved as a result of differences in boiling points of components in the stream of hydrocarbon mixture. The differences in boiling points between co-dimer and trimer impurities of dicyclopentadiene are relatively small, thus it is very energy intensive to achieve purities of dicyclopentadiene above 94% by weight using fractional distillation.

In view of the forgoing, an objective of the present invention is to provide a dynamic process for purifying dicyclopentadiene from a mixed liquid hydrocarbon stream comprising $C_5$ compounds, dimers, co-dimers, and various minor organic impurities by melt crystallizing, sweating, and collecting dicyclopentadiene.

BRIEF SUMMARY OF THE INVENTION

According to a first aspect, the present disclosure relates to a dynamic method for purifying dicyclopentadiene from a mixed liquid hydrocarbon stream, involving i) delivering at least a portion of the mixed liquid hydrocarbon stream to an inlet port of a separation/purification unit, wherein the mixed liquid hydrocarbon stream comprises dicyclopentadiene and one or more of a $C_5$ paraffin, a $C_5$ olefin, co-dimers, cyclopentadiene, benzene, vinyl norbornene, bicyclononadiene, propenyl norbornene, isopropenyl norbornene, methylbicyclononadiene, methyldicyclopentadiene, and various minor organic impurities, ii) dividing the mixed liquid hydrocarbon stream to form a plurality of mixed liquid hydrocarbon streams and flowing the plurality of mixed liquid hydrocarbon streams through a low temperature region of the separation/purification unit, iii) continuously contacting the plurality of mixed liquid hydrocarbon streams with an inner wall of the separation/purification unit to form an impure crystalline slurry comprising an impure crystalline phase, and an excess liquid phase, wherein dicyclopentadiene crystals are present in the impure crystalline phase, iv) depositing the impure crystalline phase on the inner wall of the separation/purification unit, v) recycling at least a portion of the excess liquid phase to the inlet port of the separation/purification unit, vi) sweating the impure crystalline phase at least once to a sweating temperature to at least partially melt the impure crystalline phase and/or an low melting impurity present in the impure crystalline phase to form a purified crystalline phase comprising the dicyclopentadiene crystals and a molten impurity phase and separating the molten impurity phase from the purified crystalline phase, vii) melting the dicyclopentadiene crystals in the purified crystalline phase on the inner wall of the separation/purification unit to form molten dicyclopentadiene and collecting the molten dicyclopentadiene.

In one embodiment, the dynamic method further comprises delivering the molten dicyclopentadiene to a second separation/purification unit located downstream of the separation/purification unit to produce the molten dicyclopentadiene having purity of at least 90%.

In one embodiment, the impure crystalline phase is sweated once to form the purified crystalline phase and the molten impurity phase.

In one embodiment, the impure crystalline phase is sweated more than once to form the purified crystalline phase and the molten impurity phase, wherein the sweating temperature is increased for each sweating operation relative to a previous sweating temperature.

In one embodiment, the dynamic method with multiple sweating produces the molten dicyclopentadiene having a purity that is higher than a substantially similar process where the impure crystalline phase is sweated once.

In one embodiment, the dynamic method further comprises removing impurities to supersaturate the mixed liquid hydrocarbon stream prior to the delivering.

In one embodiment, the mixed liquid hydrocarbon stream comprises 75% to 95% dicyclopentadiene by weight prior to the delivering.

In one embodiment, the excess liquid phase comprises an impure fraction and the method further comprises purging the impure fraction from the excess liquid phase prior to the recycling to form a purged impure fraction.

In one embodiment, the dynamic method further comprises fractionally distilling the purged impure fraction with a distillation column to recover a residual dicyclopentadiene.

In one embodiment, the dynamic method further comprises combining the residual dicyclopentadiene with the molten dicyclopentadiene to give a final yield of dicyclopentadiene that is higher than a method without combining.

In one embodiment, the dynamic method further comprises purifying the molten impurity phase with an auxiliary separation/purification unit to recover molten dicyclopentadiene from the molten impurity phase.

In one embodiment, the dynamic method further comprises combining the molten dicyclopentadiene from the auxiliary separation/purification unit with the molten dicyclopentadiene from the separation/purification unit to give a final yield of dicyclopentadiene that is higher than a method without combining.

In one embodiment, the dynamic method further comprises collecting the excess liquid phase in a reservoir located downstream of the separation/purification unit and recycling at least a portion of the excess liquid phase from the reservoir to the inlet port of the separation/purification unit.

In one embodiment, the dynamic method is performed in a temperature range of 0 to 40° C.

According to a second aspect, the present disclosure relates to a cascade process for purifying dicyclopentadiene from a mixed liquid hydrocarbon stream, involving i) delivering at least a portion of the mixed liquid hydrocarbon stream to an inlet port of a first separation/purification unit, wherein the mixed liquid hydrocarbon stream comprises dicyclopentadiene and one or more of a $C_5$ paraffin, a $C_5$ olefin, co-dimers, cyclopentadiene, benzene, vinyl norbornene, bicyclononadiene, propenyl norbornene, isopropenyl norbornene, methylbicyclononadiene, and methyldicyclopentadiene, ii) dividing the mixed liquid hydrocarbon stream to form a plurality of mixed liquid hydrocarbon streams and flowing the plurality of mixed liquid hydrocarbon streams through a low temperature region of the first separation/purification unit, iii) continuously contacting the plurality of mixed liquid hydrocarbon streams with an inner wall of the first separation/purification unit to form an impure crystalline slurry comprising an impure crystalline phase, and an excess liquid phase, wherein dicyclopentadiene crystals are present in the impure crystalline phase, iv) depositing the impure crystalline phase on the inner wall of the first separation/purification unit, v) recycling at least a portion of the excess liquid phase to the inlet port of the first separation/purification unit, vi) sweating the impure crystalline phase at least once to a sweating temperature to at least partially melt the impure crystalline phase and/or a low melting impurity present in the impure crystalline phase to form a purified crystalline phase comprising the dicyclopentadiene crystals and a molten impurity phase and separating the molten impurity phase from the purified crystalline phase, vii) melting the dicyclopentadiene crystals in the purified crystalline phase on the inner wall of the first separation/purification unit to form a first molten dicyclopentadiene, viii) delivering the first molten dicyclopentadiene to a second separation/purification unit located downstream of the first separation/purification unit and repeating the dividing, the continuously contacting, the depositing, the recycling, the sweating, and the melting in the second separation/purification unit to form a second molten dicyclopentadiene that has a higher purity than the first molten dicyclopentadiene.

According to a third aspect, the present disclosure relates to a fractional crystallization apparatus which includes i) a crystallizer including ia) an elongated tube with at least one inlet port located at a first end of the elongated tube and at least one outlet port located at a second end of the elongated tube, ib) a heat exchanger that jackets the elongated tube, ic) a septum located inside the elongated tube and adjacent to the at least one inlet port, id) a temperature sensor located close to the at least one outlet port, ii) a reservoir located downstream of the crystallizer and fluidly connected to the elongated tube through the at least one outlet port by an outlet line and at least one valve, iii) a pump fluidly connected to the reservoir and the at least one inlet port through a recycle line, wherein the crystallizer separates a liquid hydrocarbon mixture to form dicyclopentadiene and an excess liquid phase, the septum distributes the liquid hydrocarbon mixture comprising dicyclopentadiene to an inner wall of the elongated tube, the reservoir collects the excess liquid phase, and the pump recycles the excess liquid phase from the reservoir to the inlet port of the crystallizer.

In one embodiment, the fractional crystallization apparatus further comprises an agitator located in the reservoir to prevent crystallization of the excess liquid phase.

In one embodiment, the fractional crystallization apparatus further comprises an orifice plate located inside the elongated tube and downstream of the at least one inlet port and upstream of the septum to control a flow rate of the liquid hydrocarbon mixture.

In one embodiment, the fractional crystallization apparatus further comprises a cylindrical mesh attached to the inner wall of the elongated tube, wherein the cylindrical mesh increases a contact surface between the liquid hydrocarbon mixture and the crystallizer to facilitate dicyclopentadiene crystal nucleation.

In one embodiment, the septum is perforated and distributes the liquid hydrocarbon mixture as a plurality of liquid hydrocarbon streams onto the cylindrical mesh to increase a contact surface.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
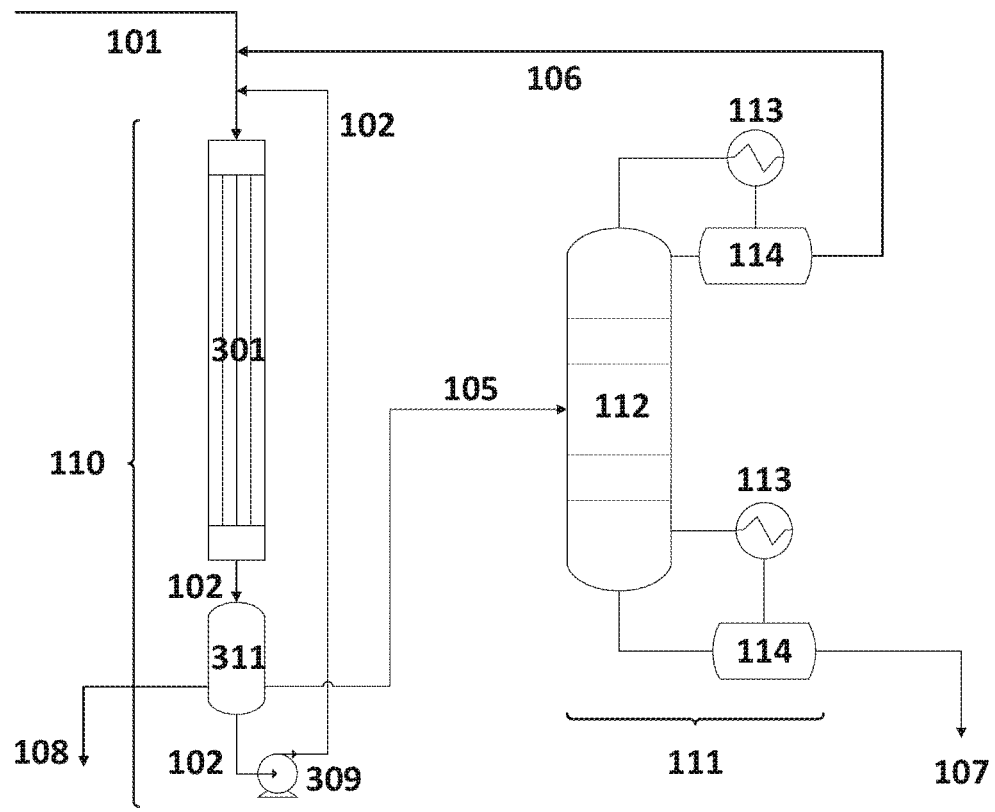
FIG. 1 is a Process Flow Diagram (PFD) of the dynamic process for purifying dicyclopentadiene from the mixed liquid hydrocarbon stream using melt crystallization.

Referring now to the drawings, wherein like reference numerals designate identical or corresponding parts throughout the several views.

Referring now to FIG. 1. According to a first aspect, the present disclosure relates to a dynamic method for purifying dicyclopentadiene from a mixed liquid hydrocarbon stream 101, involving delivering at least a portion of the mixed liquid hydrocarbon stream to an inlet port of a separation/purification unit 110.

The mixed liquid hydrocarbon stream of the present disclosure is a mixture of dicyclopentadiene and one or more of the following organic compounds: a $C_5$ paraffin, a $C_5$ olefin, co-dimers, cyclopentadiene, benzene, vinyl norbornene, bicyclononadiene, propenyl norbornene, isopropenyl norbornene, methylbicyclononadiene, methyldicyclopentadiene, and various minor organic impurities. Other hydrocarbon materials may be present in the mixed liquid hydrocarbon stream including solvents and/or carrier materials having a boiling point higher than the boiling point of dicyclopentadiene. Preferably the mixed liquid hydrocarbon stream is a liquid stream of organic hydrocarbons that is substantially free of an aqueous phase and/or contains substantially no water.

The mixed liquid hydrocarbon stream may be produced by reforming a variety of feedstocks, including petroleum crude oil, natural gas, etc. The reforming process may include cracking, destructive distillation, pyrolysis, hydrotreatment, and the like and therefore the mixed liquid hydrocarbon stream may come from a cracking unit, a distillation column, a hydrotreatment unit, or any other process that can produce dicyclopentadiene as a byproduct. The mixed liquid hydrocarbon stream may comprise one or more $C_5$ compounds, dimers, co-dimers, and various minor organic compounds generally obtained through reforming of fossil fuel feedstocks (e.g. petroleum crude oil). Other hydrocarbon materials have more than 5 carbon atoms may also be present but if present are preferably present in an amount of less than 5%, preferably less than 1% or less than 0.5% by weight based on the total weight of the mixed liquid hydrocarbon stream. Cracking is a chemical process wherein complex organic molecules such as aliphatic and/or aromatic hydrocarbon compounds are broken down into simpler molecules such as light hydrocarbons and olefins by breaking of carbon-carbon bonds. This chemical process is carried out either by thermal energy (thermal cracking) or by using a catalyst (catalytic cracking). Catalytic cracking generally produces more gasoline with a higher octane rating, and more olefinic byproducts, and hence is preferred over thermal cracking.

Figure 3:
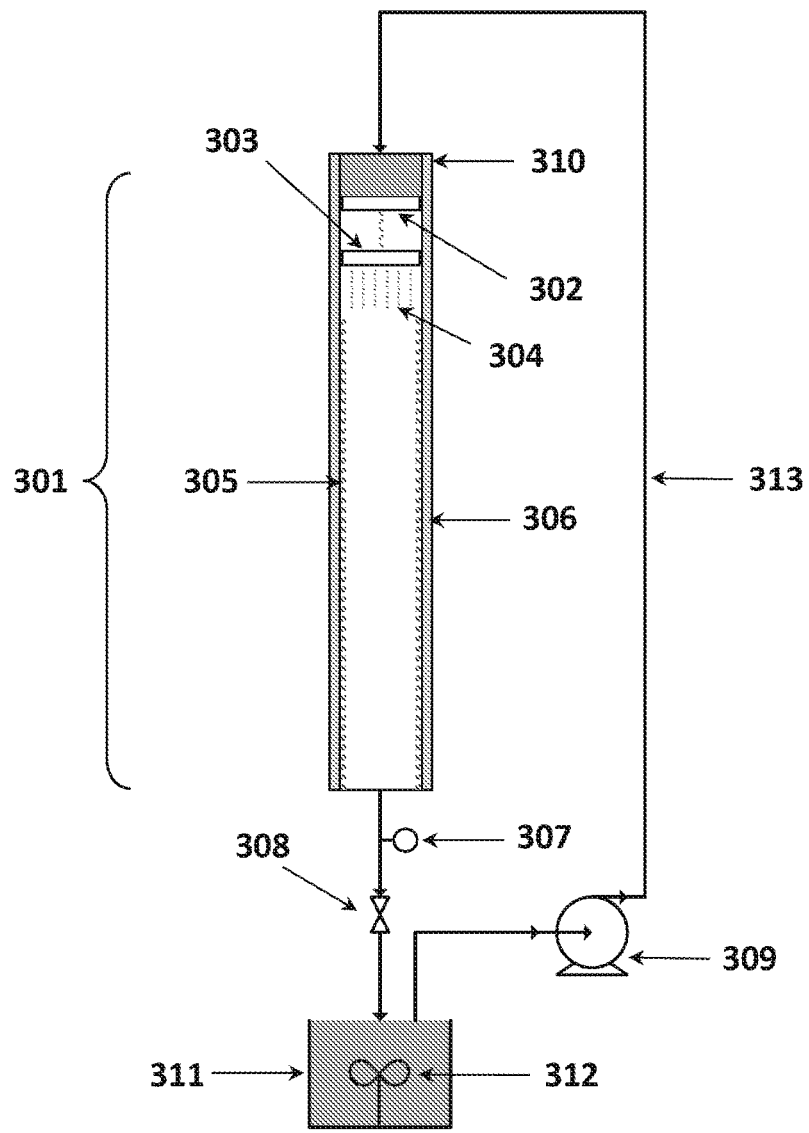
FIG. 3 is a melt crystallization set-up (separation/purification unit) which is operated in dynamic mode. The elongated tube, the heat exchanger that jackets the elongated tube, the reservoir, the circulating pump, the pipes, the valve, the cylindrical mesh, and the septum are shown in this schematic representation of the melt crystallization set-up.

The dynamic method involves dividing the mixed liquid hydrocarbon stream to form a plurality of mixed liquid hydrocarbon streams 304 and flowing the plurality of mixed liquid hydrocarbon streams 304 through a low temperature region of the separation/purification unit (as depicted in FIG. 3). The mixed liquid hydrocarbon stream can be divided into a plurality of mixed liquid hydrocarbon streams by passing the mixed liquid hydrocarbon streams through a perforated disc-shaped septum but may be of any geometry that sufficiently and/or preferably seals and/or mates the elongated tube 310. The mixed liquid hydrocarbon stream may also be divided into a plurality of mixed liquid hydrocarbon streams using a liquid flow sprinkler (as described in U.S. Pat. No. 4,560,108A), or a liquid flow divider (as described in U.S. Pat. No. 4,085,776A), or any device that divides a liquid stream into a plurality of streams.

The dynamic method further involves continuously contacting the plurality of mixed liquid hydrocarbon streams with an inner wall of the separation/purification unit. Impure crystalline slurry comprising an impure crystalline phase and an excess liquid phase 102 is formed as a result of the continuously contacting. The impure crystalline phase is deposited on the inner wall of the separation/purification unit, while the excess liquid phase flows out of the separation/purification unit.

Continuous contacting refers to a process whereby the plurality of mixed liquid hydrocarbon streams is flowed from top to bottom onto the inner wall of the separation/purification unit such that the flowing liquid makes contact with at least 70% of the total height and/or area of the inner wall as the liquid streams flow downward. Continuous contacting requires that at least a portion of the flowing liquid is in contact with the inner wall during the process. Continuous contacting does not require that the entire volume or amount of the flowing liquid is always in contact with the inner wall. Continuous contacting is different than non-continuous contacting in that continuous contacting requires a flow of a mixed liquid hydrocarbon stream, while non-continuous contacting does not involve flowing the liquid streams. For example, non-continuous contacting may refer to a method whereby a separation/purification unit is filled with a liquid or a gas, and the liquid or the gas is contacted with only a portion of the inner wall of the separation/purification unit over time.

The low temperature region is a section of the separation/purification unit comprising an elongated tube which may be jacketed by a heat exchanger. The low temperature region of the separation/purification unit reduces temperature of the liquid stream which is in direct contact with it. In one embodiment, 10%-100%, preferably 50%-90%, more preferably 60%-80%, and even more preferably 70% of total height and/or area of the elongated tube may be jacketed with the heat exchanger, and therefore the low temperature region for example constitutes at least 70% of the elongated tube. The low temperature region of the separation/purification unit may be controlled by a computer-controlled cooling unit wherein coolant, which can be an aqueous glycol solution, water, a fluorocarbon, and the like is circulated in the heat exchanger and lowers the temperature of the inner wall of the separation/purification unit at a cooling ramp rate in a range of 0.6-2.4° C./hr, preferably 0.6-1.8° C./hr, and more preferably 0.6-1.2° C./hr to a cooling temperature in a range of 4° C.-10° C., or 5° C.-9° C., or 6° C.-8° C., or about 7° C.

In one embodiment, before the dividing the mixed liquid hydrocarbon stream has an initial temperature range of 18° C.-26° C., or 20° C.-24° C., or about 22° C. Since the mixed liquid hydrocarbon stream may be supplied from a reforming process that generally occurs at elevated temperatures, the mixed liquid hydrocarbon stream may be cooled to this initial temperature by passing through a cooling unit prior to the delivering. In one embodiment, the cooling unit may include air coolers having rotating fans located across from a feed line, wherein the rotating fans cool the mixed liquid hydrocarbon stream flowing through the feed line.

In one embodiment, for large scale applications such as pilot plants and/or manufacturing plants delivering the mixed liquid hydrocarbon stream is carried out with a flow rate in a range of 1 l/min-100 l/min, preferably 10 l/min-60 l/min, and even more preferably 30 l/min-40 l/min, whereas for small scale applications such as laboratory set-up the mixed liquid hydrocarbon stream is carried out with a flow rate in a range of 10 ml/min-60 ml/min, preferably 15 ml/min-40 ml/min, more preferably 20 ml/min-30 ml/min, and even more preferably 25 ml/min.

The dynamic method further comprises depositing the impure crystalline phase on the inner wall of the separation/purification unit. Depositing refers to a process whereby the impure crystalline phase is preferably nucleating on the inner wall of the separation/purification unit and crystallization is preferably occurring thereafter.

In one embodiment, the dynamic method further comprises collecting the excess liquid phase in a reservoir located downstream of the separation/purification unit and recycling at least a portion of the excess liquid phase from the reservoir to the inlet port of the separation/purification unit.

In one embodiment, the excess liquid phase in the reservoir may be heated prior to the recycling. Heating the excess liquid phase may remove some volatile impurities and supersaturate the excess liquid phase with for example dicyclopentadiene. A crystallization process includes at least two steps and is preferably a two-step phenomenon that includes steps of nucleation and crystal growth. In the nucleation, dispersed crystallizing molecules in a mixture aggregate and form nuclei. Formed nuclei continue growing until large crystals form. In crystallization, super-saturation is a driving force, because it determines rate of nucleation and rate of crystal growth. Once super-saturation is exhausted, the crystalline phase and liquid phase reach equilibrium and the crystallization is complete, unless further operations bring the mixture to super-saturation conditions.

In one embodiment, the excess liquid phase comprises an impure fraction that may comprise one or more of a $C_5$ paraffin, a $C_5$ olefin, cyclopentadiene, benzene, vinyl norbornene, bicyclononadiene, propenyl norbornene, isopropenyl norbornene, methylbicyclononadiene, methyldicyclopentadiene, co-dimers and other components having less than 5 or more than 5 carbon atom, and the method further comprises purging the impure fraction from the excess liquid phase prior to the recycling to form a purged impure fraction 105.

In one embodiment, at least a portion of the purged impure fraction 105 comprising dimer and co-dimer impurities may be processed in separate operations (i.e. distillation columns) to recover valuable chemical compounds such as benzene, or vinyl norbornene, or bicyclononadiene, or propenyl norbornene, or isopropenyl norbornene, or methylbicyclononadiene, or methyldicyclopentadiene and to minimize waste. Since the mixed liquid hydrocarbon stream comprises a mixture of valuable organic compounds, the purged impure fraction may be delivered to a fractional distillation column, or a liquid-liquid extraction column depending on types of organic compounds present in the purged impure fraction. For instance in one embodiment, the purged impure fraction which comprises dicyclopentadiene is delivered to an auxiliary fractional distillation column 111 downstream of the separation/purification unit. The auxiliary fractional distillation column comprises a column 112 two heat exchangers 113 and two reservoirs 114 at overhead and bottom of the column. A distilled dicyclopentadiene 106 is collected from an overhead of the auxiliary fractional distillation column. In one embodiment, the distilled dicyclopentadiene 106 may be delivered to the separation/purification unit for further purifications. Other valuable chemical compounds such as benzene, or vinyl norbornene, or bicyclononadiene, or propenyl norbornene, or isopropenyl norbornene, or methylbicyclononadiene, or methyldicyclopentadiene may also be collected from an effluent 107 that flows out of the auxiliary fractional distillation column.

The dynamic method also involves sweating the impure crystalline phase. The sweating comprises partially melting the impure crystalline phase to form a purified crystalline phase and a molten impurity phase.

The molten impurity phase may then flow out of the separation/purification unit, leaving behind the purified crystalline phase. The molten impurity phase may comprise dicyclopentadiene in a major or minor amount, preferably in an amount of less than 40%, 30%, 20% or 10% by weight based on the total weight of the molten impurity phase.

The sweating involves raising the temperature of the inner wall of the separation/purification unit at a sweating ramp rate to a sweating temperature to melt the impure crystalline phase occluded, adsorbed and/or co-crystallized in the dicyclopentadiene crystals, wherein the molten impurity phase is separated from the purified crystalline phase and collected at the bottom of the separation/purification unit in the reservoir.

In one embodiment, the molten impurity phase is separated from the purified crystalline phase by gravity (i.e. allowing the molten impurity phase to drip or sweat off of the purified crystalline phase), or by centrifugal force (i.e. centrifuge), or by entrainment of the molten impurity phase into a carrier gas, or by liquid washing, or by agitation (i.e. shaking, rotating, stirring, etc.).

The sweating temperature at which the impure crystalline phase melts is always below melting point of the dicyclopentadiene crystals which is around 33.6° C. The sweating temperature may be in a range of 8° C.-33° C., preferably 20° C.-30° C., and more preferably 23° C.-27° C. The sweating ramp rate at which temperature of the inner wall of the separation/purification unit is raised may be in a range of 0.6° C./hr-3° C./hr, preferably 1° C./hr-2.8° C./hr, and more preferably 2° C./hr-2.5° C./hr.

In one embodiment, the impure crystalline phase is sweated once to form the purified crystalline phase and the molten impurity phase.

In one embodiment, the impure crystalline phase is sweated more than once to form the purified crystalline phase and the molten impurity phase.

Depending on initial content of dicyclopentadiene in the mixed liquid hydrocarbon stream, one or more sweating operations may be required to obtain purified crystalline phase with desirable purity for example a purity of 90%-99%, preferably 94%-99%, and more preferably 97%-99%. For example, for a mixed liquid hydrocarbon stream comprised of 93% dicyclopentadiene by weight, at least two sweating operations may be required to yield a purified crystalline phase of at least 97% dicyclopentadiene by weight. In the case of multiple sweating operations, the sweating temperature may be increased while the sweating ramp rate may be decreased for each sweating operation relative to a previous sweating temperature and a previous sweating ramp rate. For example, an inner wall of a separation/purification unit may initially have a temperature of 7° C., and a mixed liquid hydrocarbon stream flowing out of the separation/purification unit may have a temperature of 13° C. For a first sweating, the temperature of the inner wall of the separation/purification unit may be raised to 23° C. and the molten impurity phase may be collected over a period of 1 hour. For a second sweating, the temperature of the inner wall of the separation/purification unit may be raised to 27° C. and the molten impurity phase may be collected over a period of 45 minutes.

In one embodiment, the dynamic method that involves multiple sweating operations produces the molten dicyclopentadiene having a purity that is higher than a substantially similar process where the impure crystalline phase is sweated once. For example, purity of the molten dicyclopentadiene which is produced from a process that involves at least two sweating operations is at least 1%, or at least 3% or at least 5% greater than a corresponding impure crystalline phase that is sweated only once.

In one embodiment, a liquid washing may be performed after the sweating for separating the molten impurity phase from the purified crystalline phase. An organic solvent that is preferably immiscible in dicyclopentadiene which can dissolve organic impurities may be used in the liquid washing. For example, ethanol, isopropanol, acetone, n-hexane, toluene, and the like may be used as the organic solvent. Other organic solvent that are useful for washing the purified crystalline phase include low boiling organic materials such as propane, propene, n-butane, iso-butane, sec-butane, butane, and the like. In one embodiment, the separation/purification unit is filled with the organic solvent and remained in static condition (i.e. without motion) over time. In one embodiment, the organic solvent is sprayed onto the molten impurity phase/purified crystalline phase under pressure. The organic impurities in the dicyclopentadiene crystals may diffuse and dissolve in the organic solvent. The organic solvent that now contains the molten impurity phase may then be drained from the separation/purification unit leaving behind the purified crystalline phase comprising dicyclopentadiene crystals. Residues of the low boiling hydrocarbon wash used to purify the impure crystalline phase may be removed from the purified crystalline phase by distillation or evaporation.

In one embodiment, a compressed dry air or inert gas such as nitrogen may be flowed over the purified crystalline phase after the liquid washing for separating moisture and other volatile compounds from the purified crystalline phase. The compressed dry air may be supplied by a compressor and an air cooling system.

In one embodiment, the dynamic method further comprises purifying the molten impurity phase with an auxiliary separation/purification unit to recover molten dicyclopentadiene from the molten impurity phase. In one embodiment, the dynamic method further comprises combining the molten dicyclopentadiene from the auxiliary separation/purification unit with the molten dicyclopentadiene from the separation/purification unit to give a final yield of dicyclopentadiene that is higher than a method without the combining.

The dynamic method also preferably involves melting the dicyclopentadiene crystals on the inner wall of the separation/purification unit to form molten dicyclopentadiene 108 and collecting the molten dicyclopentadiene.

The melting comprises raising the temperature of the inner wall of the separation/purification unit to a melting temperature, wherein the melting temperature is at least 5° C., or at least 6° C., or at least 7° C., or at least 8° C., or at least 9° C., or at least 10° C. higher than the sweating temperature, or in the case of multiple sweating operations, the most recent sweating temperature.

In one embodiment, the process of purifying may be used for separating and purifying other types of organic compounds by adjusting processing variables such as the cooling rate, the sweating temperature, the melting temperature, and more importantly the cooling temperature. For example benzene, benzoic acid, dichlorobenzene, nitrochlorobenzene, bisphenol A, xylene, naphthalene, hydrazine, cresol, or caprolactam may be separated and purified using the dynamic method.

In one embodiment, the dynamic method further comprises pre-purifying the mixed liquid hydrocarbon stream prior to the delivering. A coarse purifying prior to the delivering may significantly reduce the number of the separation/purification units required for purification. Therefore, the mixed liquid hydrocarbon stream may be delivered to an auxiliary distillation column located upstream of the separation/purification unit, and distilled cyclopentadiene may be collected from an overhead of the auxiliary distillation column. The distilled cyclopentadiene may be further dimerized to form dicyclopentadiene under controlled reaction conditions in a reactor located downstream of the auxiliary distillation column and upstream of the separation/purification unit. The dicyclopentadiene formed in the dimerization reactor may then be mixed with the mixed liquid hydrocarbon stream after distillation, and the mixed streams may then be delivered to the separation/purification unit for further purification and processing.

In the present disclosure melt crystallization occurs in a temperature range of 0° C. to 40° C., preferably 0 to 20° C., more preferably 2 to 15° C., and even more preferably 6 to 12° C. to separate dicyclopentadiene from other impurities. The temperature range may depend on initial content of dicyclopentadiene and organic impurities in the mixed liquid hydrocarbon stream. Due to lower operational temperatures, the dynamic method for purifying dicyclopentadiene requires simple and inexpensive process equipment and also less safety precautions compared to conventional processes of separation and purification of dicyclopentadiene. In addition, thermal degradations and formation of undesirable byproducts may be reduced using the method disclosed herein.

In one embodiment, the mixed liquid hydrocarbon stream comprises 75% to 95%, preferably 85% to 95%, and more preferably 90% to 95% dicyclopentadiene by weight prior to the delivering. It is advantageous for the mixed liquid hydrocarbon stream to have a purity of at least 90% dicyclopentadiene by weight for economic reasons and operational costs.

In one embodiment, the dynamic method further comprises delivering the molten dicyclopentadiene to a second separation/purification unit located downstream of the separation/purification unit to produce the molten dicyclopentadiene having a purity of 90%-99%, preferably 94%-99%, and more preferably 97%-99%. At least three separation/purification units may be needed if the mixed liquid hydrocarbon stream has a purity of less than 90% dicyclopentadiene by weight and a purity of about 99% is desired in the molten dicyclopentadiene.

Figure 2:
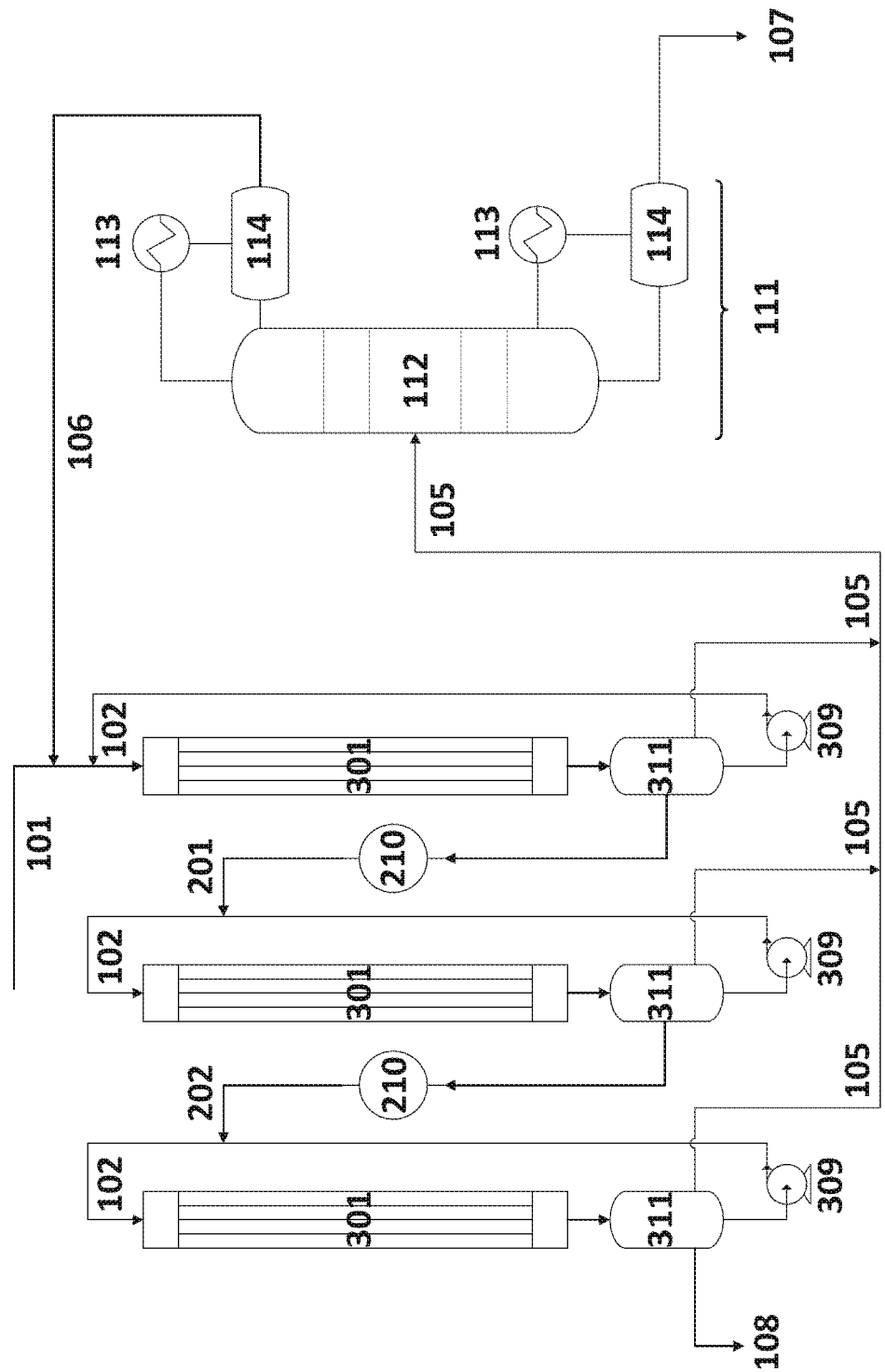
FIG. 2 is a Process Flow Diagram (PFD) of the cascade process for purifying dicyclopentadiene from the mixed liquid hydrocarbon stream comprised of three similar melt crystallizers located in series (separation/purification units) and one distillation column.

Referring now to FIG. 2. According to a second aspect, the present disclosure relates to a cascade process for purifying dicyclopentadiene from a mixed liquid hydrocarbon stream 101, involving i) delivering at least a portion of the mixed liquid hydrocarbon stream to a first separation/purification unit, wherein the mixed liquid hydrocarbon stream comprises dicyclopentadiene and one or more of a $C_5$ paraffin, a $C_5$ olefin, cyclopentadiene, benzene, vinyl norbornene, bicyclononadiene, propenyl norbornene, isopropenyl norbornene, methylbicyclononadiene, methyldicyclopentadiene, and co-dimers, ii) dividing the mixed liquid hydrocarbon stream to form a plurality of mixed liquid hydrocarbon streams and flowing the plurality of mixed liquid hydrocarbon streams through a low temperature region of the first separation/purification unit, iii) continuously contacting the plurality of mixed liquid hydrocarbon streams with an inner wall of the first separation/purification unit to form an impure crystalline slurry comprising an impure crystalline phase, and an excess liquid phase 102, wherein dicyclopentadiene crystals are present in the impure crystalline phase, iv) depositing the impure crystalline phase on the inner wall of the first separation/purification unit, v) recycling at least a portion of the excess liquid phase 102 to the inlet port of the first separation/purification unit, vi) sweating the impure crystalline phase at least once to a sweating temperature to at least partially melt the impure crystalline phase to form a purified crystalline phase comprising the dicyclopentadiene crystals and a molten impurity phase and separating the molten impurity phase from the purified crystalline phase, vii) melting the dicyclopentadiene crystals on the inner wall of the first separation/purification unit to form a first molten dicyclopentadiene 201, viii) delivering the first molten dicyclopentadiene to a second separation/purification unit located downstream of the first separation/purification unit using a pump 210 and repeating the dividing, the continuously contacting, the depositing, the recycling, the sweating, and the melting in the second separation/purification unit to form a second molten dicyclopentadiene 202 that has a higher purity than the first molten dicyclopentadiene.

In one embodiment, the first molten dicyclopentadiene is collected in a first container located downstream of the first separation/purification unit and upstream of the second separation/purification unit. The first molten dicyclopentadiene in the first container is delivered to the second separation/purification unit using a circulation pump 210. The second molten dicyclopentadiene is collected in a second container located downstream of the second separation/purification unit and upstream of a third separation/purification unit. The second molten dicyclopentadiene in the second container is delivered to the third separation/purification unit using another circulation pump, and the dividing, the continuously contacting, the depositing, the recycling, the sweating, and the melting is performed in the third separation/purification unit.

Depending on the initial content of dicyclopentadiene in the mixed liquid hydrocarbon stream and the desired content of dicyclopentadiene in final purified product, multiple separation/purification units may be needed. Although it is technically feasible to use the dynamic method for purifying the mixed liquid hydrocarbon stream of any content of dicyclopentadiene, it may be preferred to start with a stream of having at least 85% dicyclopentadiene by weight to be economically viable. For instance, at least 3 or 4 or 5 separation/purification units may be required to purify a mixed liquid hydrocarbon stream of having at least 85%, or at least 86%, or at least 87%, or at least 88%, or at least 89%, or at least 90% dicyclopentadiene by weight to a stream having a purity of at least 97%, or at least 98%, or at least 99% dicyclopentadiene by weight as final product. More than 5 separation/purification units may be required to purify the mixed liquid hydrocarbon stream having a purity less than 85% dicyclopentadiene by weight.

In one embodiment, the cascade process for purifying dicyclopentadiene further comprises recycling at least a portion of product stream 108 (as depicted in FIG. 2), to the inlet port of the first separation/purification unit in the cascade process.

Referring now to FIG. 3. According to a third aspect, the present disclosure relates to a fractional crystallization apparatus 110 which includes a crystallizer 301 that separates the mixed liquid hydrocarbon stream to form dicyclopentadiene crystals and the excess liquid phase.

As used herein, the "fractional crystallization apparatus" also refers to the "separation/purification unit" and therefore these terms can be used interchangeably.

The crystallizer comprises an elongated tube 310 with at least one inlet port located at a first end of the elongated tube and at least one outlet port located at a second end of the elongated tube. The elongated tube may comprise glass and/or metal. The elongated tube may be cylindrical in shape, and may be positioned horizontally or vertically, although the preferred design may be a vertical cylindrical glass elongated tube. The second end of the elongated tube may be tapered or non-tapered. A tapered end may ease collecting any liquid phase that flows out of the elongated tube, and therefore in a preferred embodiment the second end of the elongated tube is tapered. Size of the elongated tube for small scale applications such as laboratory set up may be at most 100 cm in length (L) and at most 1.9-2.5 cm in inner diameter (D). Relative ratio of tube length to inner diameter (L/D) for the elongated tube for small scale applications may be in the range of 30-70, preferably 30-50, and more preferably about 40. Relative ratio of tube length to inner diameter (L/D) for the elongated tubes for large scale applications may be in the range of 50-500, preferably 100-300, and more preferably 160-240.

In one embodiment, inner wall of the elongated tube may have a rough surface. Surface roughness of the inner wall of the elongated tube may be isotropic (or patterned) and/or anisotropic (or irregular). Example of a patterned surface may be vertically or horizontally oriented channels, crosshatched, radial or circular channels, periodic concaved and convened protrusions, and the like. The average surface roughness of the inner wall of the elongated tube may be at least 100 µm, preferably 500-10,000 µm, or 1,000-5,000 µm. Formed crystals may better adhere to the rough surface and may not slipping off during the recycling and/or the sweating thereof.

The crystallizer further comprises a heat exchanger 306 that jackets at least a portion of the elongated tube. The heat exchanger may be connected to a computer-controlled cooling accessory and/or unit wherein coolant, which can be an aqueous glycol solution, water, a fluorocarbon, and the like, is circulating in the heat exchanger. The heat exchanger may be a hollow metal tube, or a helical coil that surrounds the elongated tube. In one embodiment, at least 10%-100%, preferably at least 50%-90%, more preferably at least 60%-80%, and even more preferably at least 70% of total height of the elongated tube may be jacketed with the heat exchanger.

The crystallizer further comprises a septum 303 located inside the elongated tube and adjacent to the at least one inlet port. The septum separates the mixed liquid hydrocarbon stream into a plurality of mixed liquid hydrocarbon streams 304 and distributes the plurality of mixed liquid hydrocarbon streams towards the inner wall of the elongated tube. The septum may be made of glass or metal depending on the mixed liquid hydrocarbon stream, and can be used in any shape, preferably disc shape, or cylindrical, or spherical.

In one embodiment, the septum may be a disc-shape septum and may be perforated to form the plurality of streams that provides higher contact surface with the inner wall of the elongated tube than a substantially similar septum without perforation. The perforation in the septum may be different depending on physical characteristics of the mixed liquid hydrocarbon stream such as viscosity, flow rate, etc. For instance, for low-viscous streams the septum may have a plurality of small holes like a shower head, and for high-viscous streams the septum may have fewer but larger holes, like a Swiss cheese. Position and angular direction of the septum may also be adjusted by a mechanical control mechanism which is attached to it.

In one embodiment, the septum is a disc-shape channel distributer to distribute the mixed liquid hydrocarbon stream as a plurality of stream channels that contact the inner wall of the elongated tube.

In one embodiment, more than one septum may be used at different heights of the elongated tube to distribute the mixed liquid hydrocarbon stream in different ways.

In one embodiment, a rotatory sprinkler (as described in U.S. Pat. No. 4,560,108A) may be used to separate the mixed liquid hydrocarbon stream to a plurality of streams. A convergent-divergent nozzle at the outlets of the rotatory sprinkler form stream jets and the rotatory sprinkler thrust the stream jets into the inner wall of the elongated tube.

In one embodiment, a liquid flow divider (as described in U.S. Pat. No. 4,085,776A) may be used to divide the mixed liquid hydrocarbon stream into a plurality of streams.

The crystallizer further comprises a temperature sensor 307 located downstream of the elongated tube to measures temperature of the mixed liquid hydrocarbon stream or other effluent that flows out of the crystallizer through the at least one outlet port. The temperature sensor may be a thermocouple of any kind, or a thermometer, or a temperature gauge.

The fractional crystallization apparatus further comprises a reservoir 311 located downstream of the crystallizer and fluidly connected to the elongated tube through the outlet port a transfer line and a valve, and collects the excess liquid phase. The reservoir may be made of metal, glass, or ceramic. The reservoir may be sealed or not sealed depending on the type of hydrocarbon streams used. Volume of the reservoir for small scale applications such as laboratory set up may be at most 500 ml, preferably 100-400 ml, and more preferably 200-300 ml, whereas for large scale applications such as pilot plants and/or manufacturing plants, volume of the reservoir may be at least 500 l, preferably 1,000-5,000 l, and more preferably 2,000-3,000 l.

In one embodiment, the reservoir further comprises an agitator 312 located inside the reservoir to agitate the excess liquid phase and to prevent crystallization of the excess liquid phase inside the reservoir. In one embodiment, the agitator may be a magnetic stirrer or a mechanical stirrer (i.e. a propeller). In one embodiment, the magnetic stirrer may be a magnet which is placed inside a magnetic field provided by a magnetic plate located underneath the reservoir. Angular velocity of the magnetic stirrer can be adjusted by changing intensity of the magnetic field.

In one embodiment, the magnetic plate can also provide heat (or provide cool temperatures using a cooling accessory), to adjust the temperature of the excess liquid phase in the reservoir.

The fractional crystallization apparatus further comprises a pump 309 fluidly connected to the reservoir and the inlet port of the crystallizer with transfer pipes. The pump recycles the excess liquid phase from the reservoir to the crystallizer through the inlet port. The pump may be a centrifugal, or a rotatory, or a positive displacement pump.

The fractional crystallization apparatus further comprises transfer pipes 313 to fluidly connect the crystallizer to the reservoir, the reservoir to the pump, and the pump to the crystallizer. The transfer pipes may be made of glass, plastic or metal depending on the type of hydrocarbon stream used.

In one embodiment, the transfer pipes are wrapped with flame proof heating tape to prevent crystallization and deposition inside the pipes.

In one embodiment, the excess liquid phase is heated inside the reservoir before the recycling to prevent crystallization and deposition inside the pipes.

In one embodiment, non-stick plastic tubes such as polytetrafluoroethylene (PTFE®) tubes may be used as a replacement for the transfer pipes to prevent crystallization and deposition inside the transfer pipes. Non-stick plastic tubes may provide slippery surfaces along the flow of liquid streams by reducing surface energy. Therefore, the non-stick plastic tubes may reduce the residence time of dicyclopentadiene inside of any transfer tubing/piping which may in turn reduce or prevent crystallization and deposition inside the pipes.

In one embodiment, the fractional crystallization apparatus further comprises a valve 308 located on a transfer pipe that fluidly connects the crystallizer to the reservoir. The valve may be a gate valve or a globe valve. The valve may also be used to control a flow rate of the excess liquid phase flowing out of the crystallizer.

In one embodiment, the fractional crystallization apparatus further comprises an orifice plate 302 located inside the elongated tube and downstream of the inlet port and upstream of the septum to control a flow rate of the mixed liquid hydrocarbon stream flowing inside the crystallizer. The orifice plate may be a thin circular plate, or a disc-shape plate that has a convergent-divergent hole in it. The flow rate of the mixed liquid hydrocarbon stream may be adjusted by knowing hydrostatic pressure upstream and downstream of the orifice plate. By changing the flow rate of the mixed liquid hydrocarbon stream, residence time of the mixed liquid hydrocarbon stream inside the crystallizer may be adjusted. The orifice plate may subsequently affect process time and number of recycling iterations needed to achieve desired product purity and yield. For example, a flow rate that is too high may provide a low residence time and thus may require additional recycling, while a flow rate that is too low may increase overall process times.

In one embodiment, the fractional crystallization apparatus further comprises a cylindrical mesh 305 attached to the inner wall of the elongated tube. The cylindrical mesh may increase contact surface between the mixed liquid hydrocarbon stream and the inner wall of the elongated tube in the crystallizer to extend residence time of the mixed liquid hydrocarbon stream inside the crystallizer to facilitate dicyclopentadiene crystal nucleation. The cylindrical mesh is advantageous as it may provide larger contact surface and may expedite heat transfer required for the sweating and the melting. The cylindrical mesh may also prevent the dicyclopentadiene crystals from slipping off during the recycling and the sweating.

In one embodiment, the cylindrical mesh is made of a metal with relatively high thermal conductivity such as stainless steel, copper or a copper alloys to reduce thermal lag during heat exchanging (cooling, heating) process in the heat exchanger.

In one embodiment, the meshes in the cylindrical mesh are squares of at least 1 mm$^2$ (like a screen door) and the cylindrical mesh is wrapped all the way around the inner wall of the elongated tube.

In one embodiment, the meshes in the cylindrical mesh are polygonal and/or hexagonal (like a chicken wire) with at most 40 meshes per square centimeter and the cylindrical mesh is wrapped all the way around the elongated tube.

In one embodiment, the cylindrical mesh may cover at least a portion of the inner wall of the elongated tube.

The examples below are intended to further illustrate protocols for preparing the dynamic method for purifying dicyclopentadiene using the fractional crystallization apparatus as described and further characterizing compositions of each stream, and are not intended to limit the scope of the claims.

Example 1

Melt crystallization set-up shown in FIG. 3 consists of a single wall Jacketed glass tube (300 mm length and 10 mm ID) mounted vertically with a stopcock at the bottom end. The jacket of the glass tube is connected to a constant temperature bath for circulating a coolant like an aqueous glycol solution or water with the provision of automatic programming of coolant temperature. A glass bottle (50 ml) is used as a dicyclopentadiene reservoir. A magnetic stirring assembly is used for agitating the liquid in the reservoir to ensure uniform composition of the reservoir contents. A fluid circulating pump is used for circulating the liquid from the reservoir to the top of the glass tube. A small metal (SS) disc (the septum) with a diameter that is approximately 1-2 mm smaller than the inside diameter of the glass tube is located in the overhead section of the crystallizer such that it is uniformly spaced along its circumference. The metal disc acts as a distributor for the pumped liquid to flow along the inner wall of the jacketed glass tube. A temperature sensor is located just below the tip of the stopcock at the bottom end of the glass tube to measure the temperature of the liquid that flows out. The liquid that flows out of the jacketed glass tube is directed by a tube (a transfer line) to drain into the reservoir described earlier. A suction tube (pipe) from the reservoir leads to the circulation pump described earlier. Metal tubes are wrapped with flame proof heating tape in order to prevent solid deposition in the tubes connecting the reservoir to the pump and pump to the jacketed tube.

The melt crystallization set-up described is similar to the "Sulzer" melt crystallization apparatus used to purify acrylic acid. The "Sulzer" melt crystallization apparatus is a dynamic crystallizer which is described in U.S. Pat. No. 5,504,247A.

Example 2

Experimental Procedure: In one experiment, 40.0-75.0 g of feed dicyclopentadiene was poured in the reservoir and stirred with the magnetic stirrer. The circulating pump recycled the liquid to the jacketed glass tube at a flow rate of 25.0 ml/min. The temperature ramped down from 22.0 to 7.0° C. with the ramp rates of 0.6-2.4° C./hr. The feed dicyclopentadiene liquid that was recycled to the top of the jacketed glass tube flowed along the inner wall of the jacketed glass tube and collected in the reservoir for the next recycling. The recycling as described was continued until sufficient crystals formed on the inner wall of the glass tube. The liquid level in the reservoir was monitored to get a quantitative estimate of the formed crystals. Once sufficient crystals formed in the glass tube, the pump shut down and the liquid flow stopped and residual liquid in the glass tube drained into the reservoir. The liquid that is left behind in the reservoir was collected in a separate bottle and labeled as "Mother Liquor". Subsequently, the temperature of the coolant was gradually raised to 0.1-3.0° C. The impure layers on the crystals selectively melted at this stage and the formed liquid during this process drained into a separate container labeled as "Sweat Phase". Finally, the coolant temperature was raised to 40.0° C. and crystals in the glass tube were melted and the molten crystals were collected in a separate bottle labeled as "Product".

Example 3

In the first stage crystallization, 68.62 g of dicyclopentadiene was taken as a feed. The composition of the feed material is given in Table 1. Feed dicyclopentadiene was passed through the jacketed glass tube at a flow rate of 25 ml/min. Initial set temperature of the coolant was 16.0° C. and the actual measured temperature of the liquid draining from the bottom outlet of the glass tube was 18.3° C. Coolant temperature was lowered at a rate of 1.2° C./hr. Dicyclopentadiene flow stopped when the coolant temperature reached 9.5° C. At this point, the temperature of the dicyclopentadiene flow was 13.7° C. Mother liquor was collected in a separate sample bottle and it was 48.29 g. Mother liquor composition is given in Table 2. Coolant temperature was then raised to 9.6° C. and 0.96 g of sweat phase was collected over a period of one hour. Sweat phase composition is also given in Table 3. Finally, coolant temperature was raised to 40.0° C. and 12.75 g of molten dicyclopentadiene was collected as the product in a separate bottle. The composition of the product is given in Table 4. Methyldicyclopentadiene-1,2&3 is a blend of the three isomers of methyldicyclopentadiene.

TABLE 1

Composition of feed stream

| Compound | Wt. % |
|---|---|
| co-dimer (134) | 3.29 |
| Exo-dicyclopentadiene | 0.71 |
| Endo-dicyclopentadiene | 93.07 |
| Methylbicyclononadiene | 0.72 |
| Methyldicyclopentadiene-1,2&3 | 1.25 |

TABLE 2

Composition of the mother liquor

| Compound | Wt. % |
|---|---|
| co-dimer (134) | 3.54 |
| Exo-dicyclopentadiene | 0.77 |
| Endo-dicyclopentadiene | 92.47 |
| Methylbicyclononadiene | 0.79 |
| Methyldicyclopentadiene-1,2&3 | 1.36 |

TABLE 3

Composition of the sweat phase

| Compound | Wt. % |
|---|---|
| co-dimer (134) | 3.74 |
| Exo-dicyclopentadiene | 0.79 |
| Endo-dicyclopentadiene | 92.06 |
| Methylbicyclononadiene | 0.84 |
| Methyldicyclopentadiene-1,2&3 | 1.40 |

TABLE 4

Composition of the product

| Compound | Wt. % |
|---|---|
| co-dimer (134) | 2.20 |
| Exo-dicyclopentadiene | 0.58 |
| Endo-dicyclopentadiene | 95.19 |
| Methylbicyclononadiene | 0.46 |
| Methyldicyclopentadiene-1,2&3 | 1.00 |

Example 4

Molten crystals collected from various runs in the first stage operation (as described) were mixed together to provide the feed for the second stage which was similar to the first stage. In the second stage, 34.21 g of dicyclopentadiene was taken as a starting material. The composition of feed is given in Table 5. Feed dicyclopentadiene was passed through the jacketed glass tube at a rate of 25 ml/min. Initial set temperature of the coolant was 21.0° C. and the actual measured temperature of the liquid draining from the bottom outlet of the glass tube was 20.9° C. Coolant temperature was ramped down at a rate of 0.6° C./hr. Dicyclopentadiene flow was stopped when the coolant temperature reached 19.1° C. At this point, the actual temperature of the liquid was 19.7° C. Mother liquor was collected in a separate sample bottle and it was 6.08 g. Mother liquor composition is given in Table 6. Coolant temperature was then raised to 23.0° C. and 0.92 g of sweat phase-1 was collected over a period of one hour. Coolant temperature was then raised to 27.0° C. and 1.15 g of sweat phase-2 was collected over a period of 45 minutes. Sweat phase compositions are given in Table 7 and Table 8, respectively. Finally, coolant temperature was raised to 45.0° C. and molten product was collected in a separate bottle. The quantity of the molten product was 3.73 g and the composition is given in Table 9.

TABLE 5

Composition of feed stream delivered to the second stage

| Compound | Wt. % |
|---|---|
| co-dimer (134) | 2.15 |
| Exo-dicyclopentadiene | 0.56 |
| Endo-dicyclopentadiene | 95.19 |
| Methylbicyclononadiene | 0.58 |
| Methyldicyclopentadiene-1,2&3 | 0.9 |

TABLE 6

Composition of mother liquor collected from the second stage

| Compound | Wt. % |
|---|---|
| co-dimer (134) | 2.34 |
| Exo-dicyclopentadiene | 0.60 |
| Endo-dicyclopentadiene | 94.73 |
| Methylbicyclononadiene | 0.65 |
| Methyldicyclopentadiene-1,2&3 | 0.96 |

TABLE 7

Composition of sweat phase-1 collected from the second stage

| Compound | Wt. % |
| --- | --- |
| co-dimer (134) | 2.10 |
| Exo-dicyclopentadiene | 0.56 |
| Endo-dicyclopentadiene | 95.22 |
| Methylbicyclononadiene | 0.58 |
| Methyldicyclopentadiene-1,2&3 | 0.91 |

TABLE 8

Composition of sweat phase-2 collected from the second stage

| Compound | Wt. % |
| --- | --- |
| co-dimer (134) | 1.69 |
| Exo-dicyclopentadiene | 0.49 |
| Endo-dicyclopentadiene | 96.14 |
| Methylbicyclononadiene | 0.44 |
| Methyldicyclopentadiene-1,2&3 | 0.82 |

TABLE 9

Composition of the product collected from the second stage

| Compound | Wt. % |
| --- | --- |
| co-dimer (134) | 1.06 |
| Exo-dicyclopentadiene | 0.36 |
| Endo-dicyclopentadiene | 97.41 |
| Methylbicyclononadiene | 0.26 |
| Methyldicyclopentadiene-1,2&3 | 0.66 |

TABLE 10

Composition of feed stream delivered to the third stage

| Compound | Wt. % |
| --- | --- |
| co-dimer (134) | 1.03 |
| Exo-dicyclopentadiene | 0.73 |
| Endo-dicyclopentadiene | 97.36 |
| Methylbicyclononadiene | 0.24 |
| Methyldicyclopentadiene-1,2&3 | 0.24 |

TABLE 11

Composition of mother liquor collected from the third stage

| Compound | Wt. % |
| --- | --- |
| co-dimer (134) | 1.18 |
| Exo-dicyclopentadiene | 0.78 |
| Endo-dicyclopentadiene | 96.93 |
| Methylbicyclononadiene | 0.02 |
| Methyldicyclopentadiene-1,2&3 | 0.3 |

TABLE 12

Composition of sweat phase collected from the third stage

| Compound | Wt. % |
| --- | --- |
| co-dimer (134) | 0.79 |
| Exo-dicyclopentadiene | 0.62 |
| Endo-dicyclopentadiene | 97.75 |
| Methylbicyclononadiene | 0.01 |
| Methyldicyclopentadiene-1,2&3 | 0.25 |

TABLE 13

Composition of the product collected from the third stage

| Compound | Wt. % |
| --- | --- |
| co-dimer (134) | 0.43 |
| Exo-dicyclopentadiene | 0.45 |
| Endo-dicyclopentadiene | 98.71 |
| Methylbicyclononadiene | 0.09 |
| Methyldicyclopentadiene-1,2&3 | 0.14 |

Example 5

Molten crystals collected from various runs in the second stage operation (as described) were mixed together to provide the feed for the third stage which was similar to the product of the second stage. In the third stage, 50.92 g of dicyclopentadiene was taken as a starting material. The composition of feed is given in Table 10. Feed dicyclopentadiene was passed through the jacketed glass tube at a rate of 25 ml/min. Initial set temperature of the coolant was 26° C. Coolant temperature was ramped down at a rate of 0.3° C./hr. Dicyclopentadiene flow was stopped when the coolant temperature reached 23° C. Mother liquor was collected in a separate sample bottle and it was 27.73 g. Mother liquor composition is given in Table 11. Coolant temperature was then raised to 27° C. and 1.34 g of sweat phase was collected over a period of one hour and the composition is given in Table 12. Finally, coolant temperature was raised to 40° C. and molten product was collected in a separate bottle. The quantity of the molten product was 5.62 g and the composition is given in Table 13.

Example 6

In order to get purity levels above 99% of dicyclopentadiene, a fourth stage crystallization may be needed. In the fourth stage experiment, the third stage product (molten crystals) is used as the feed. The coolant and the process temperature in the fourth stage melt crystallization should be slightly higher than that employed in the third stage. The rest of the procedure remains the same as in the first, the second, and the third stages as described.

The sweat phases and mother liquor fractions obtained in the various stages may be appropriately recycled to a separate or previous stage to increase yield of the desired dicyclopentadiene fractions, using methods well known in the practice of melt crystallization technology.

Example 7

Figure 4:
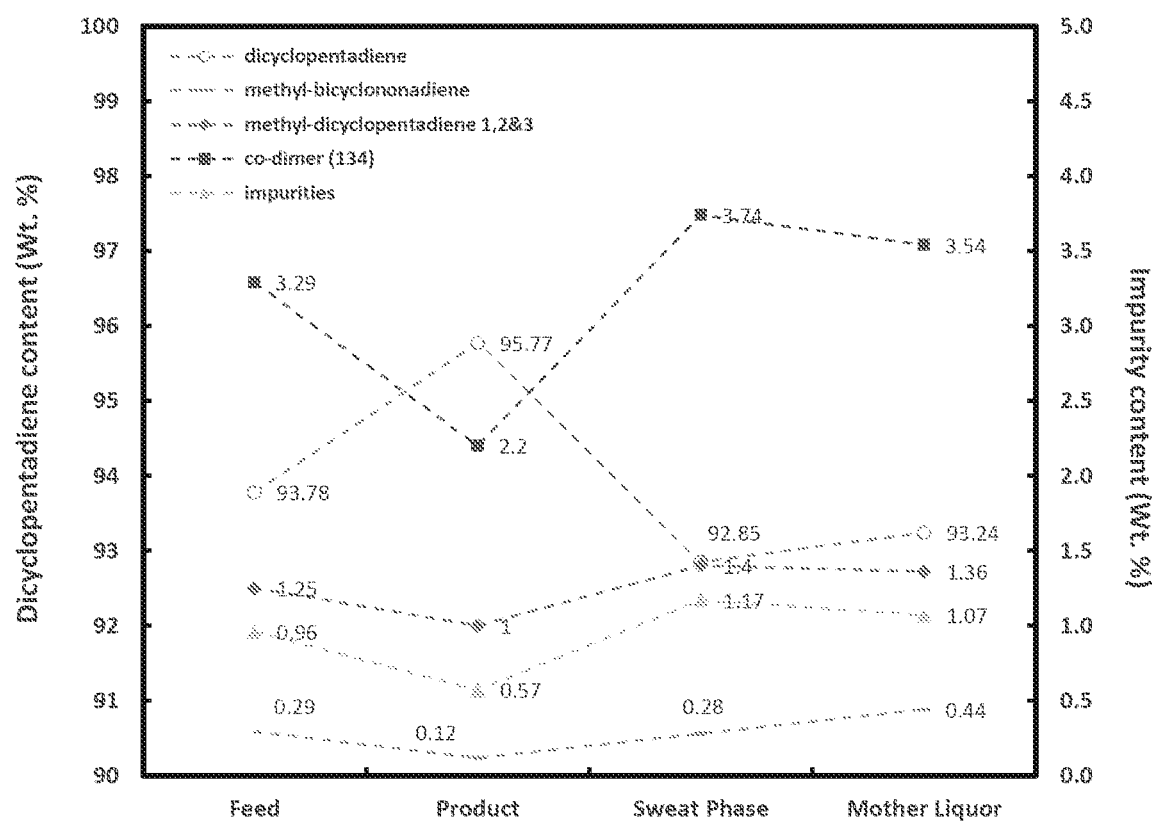
FIG. 4 represents the composition of the mixed liquid hydrocarbon stream (i.e. the feed), the molten dicyclopentadiene (i.e. the product), the molten impurity phase (i.e. the sweat phase), and the excess liquid phase (i.e. the mother liquor) during the dynamic method of purifying dicyclopentadiene in a process comprising one separation/purification unit.

FIG. 4 shows the changes in composition of the various fractions during the process of dynamic melt crystallization in one stage. The plot shows the increase of dicyclopentadiene purity and also the decrease of all other impurities such as co-dimer (134), methyl-bicyclononadiene, and methyl-dicyclopentadiene from feed to product. This chart clearly demonstrates the effectiveness of separation of impurities from crude dicyclopentadiene by the process of dynamic melt crystallization.

Figure 5A:
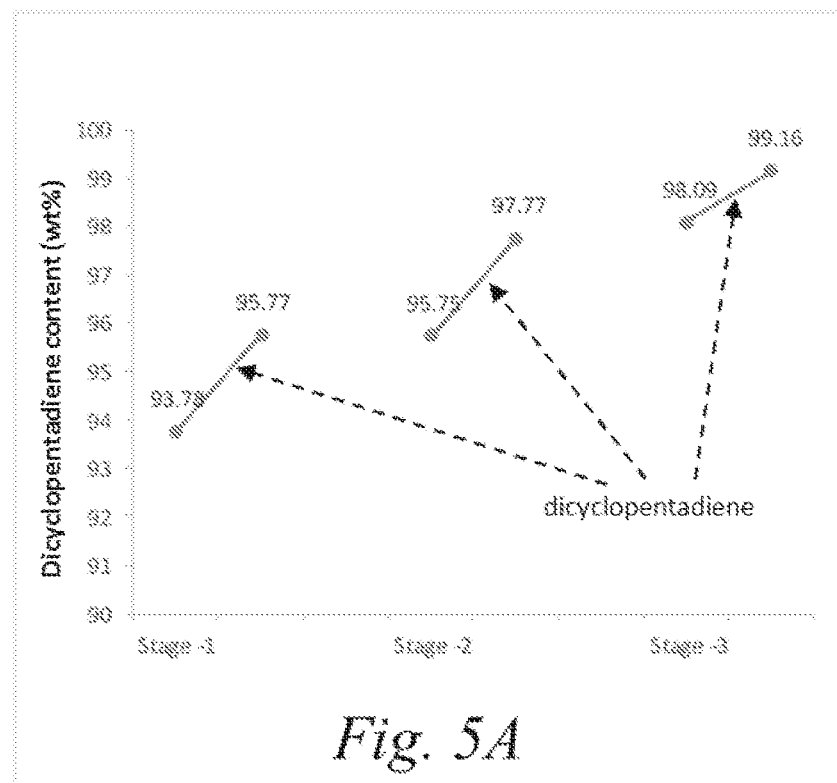
FIG. 5A represents a dicyclopentadiene content in the molten dicyclopentadiene (i.e. the product) at each stage of a three-stage purification process.

FIG. 5A shows the increase of product purity (i.e. dicyclopentadiene wt %) at each stage of a three-stage purification process. The reduction in the content of impurities at each stage of the purification process is also shown in FIG. 5B.

In lab scale experiments, the product from one stage cannot be used directly as the feed to the subsequent stage, because the amount of product produced at each stage may not be sufficient as a feed to run the subsequent stage. Therefore, product of parallel experiments at the same stage may be mixed to form the feed to the next stage. This mixing may result in a slight difference in the composition of the product from a given stage and the composition of the feed to the subsequent stage. Accordingly, the product purity vs stage number graph is shown as three discrete lines instead of a continuous line. The same logic applies to the impurity levels vs stage graph.

Figure 5B:
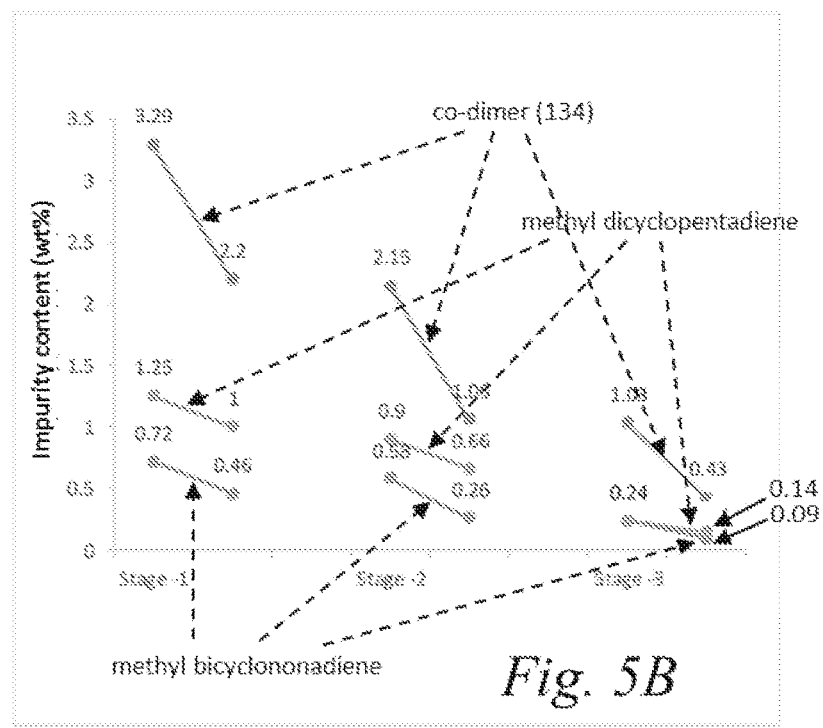
FIG. 5B represents an impurity content (i.e. co-dimer (134), methylbicyclononadiene, and methyldicyclopentadiene) in the molten dicyclopentadiene (i.e. the product) at each stage of a three-stage purification process.

The graphs of FIGS. 5A and 5B show that there is a significant increase in purity with every stage and it should be possible to attain product purities substantially above 99 wt % of dicyclopentadiene by increasing the number of stages of purification. However, as in any separation process, there would be an economic tradeoff between the product purity, investment and operating cost which would limit the maximum number of stages of purification that can be utilized.

Example 8

An experimental study to evaluate the composition of dicyclopentadiene at each stage of the dynamic melt crystallization process is provided. The composition of each sample (i.e. feed, product, sweat phase, and mother liquor) has been evaluated with a gas chromatographer utilized with a flame ionization detector (GC-FID) and a gas chromatographer utilized with a mass spectrometer (GC-MS). The concentration of dicyclopentadiene (DCPD) at each stage of the dynamic melt crystallization process was measured with respect to a certified reference standard provided by Acros Organics.

The conditions, wherein the composition of each of the samples was measured, are summarized in Table 14 and Table 15, respectively.

TABLE 14

| GC-FID experimental conditions | |
|---|---|
| Instrument | Agilent 6890N GC |
| Column | Capillary HP-5, 30 m × 0.32 mm × 0.25 μm |
| S/SL inlet temperature | 160° C. |
| Injection volume | 1.0 μL with a 10 μL syringe |
| Split ratio | 1:10 |
| Oven temperature program | Initial: 60° C. for 1 min<br>Ramp at 10° C./min to 200° C. & hold for 5 mins. |
| Detector temperature | 210° C. |
| Carrier gas and flow rate | Helium, 1.1 mL/min, constant flow mode |
| Sample preparation | 10 μL of sample diluted to 1000 μL using acetonitrile as solvent |

TABLE 15

| GC-MS experimental conditions | |
|---|---|
| Instrument | Thermo Scientific DSQ-II series Quadrupole GCMS |
| Column | Capillary HP-5, 30 m × 0.32 mm × 0.25 μm |
| S/SL inlet temperature | 160° C. |
| Injection volume | 1.0 μL with a 10 μL syringe |
| Split ratio | 1:50 |
| Oven temperature program | Initial: 60° C. for 1 min<br>Ramp at 10° C./min to 200° C. & hold for 5 min. |
| Carrier gas and flow rate | Helium, 1.1 mL/min, constant flow mode |
| Transfer line temperature | 200° C. |
| Ion source temperature | 200° C. |
| MS mode | Electron ionization, scan m/z 40 to 250 |
| Sample preparation | 10 μL of sample diluted to 1000 μL using acetonitrile as solvent |

Example 9

The composition of each sample was measured via the GC-FID and the GC-MS techniques. A representative gas chromatogram of the feed is given in FIG. 6.

Figure 6:
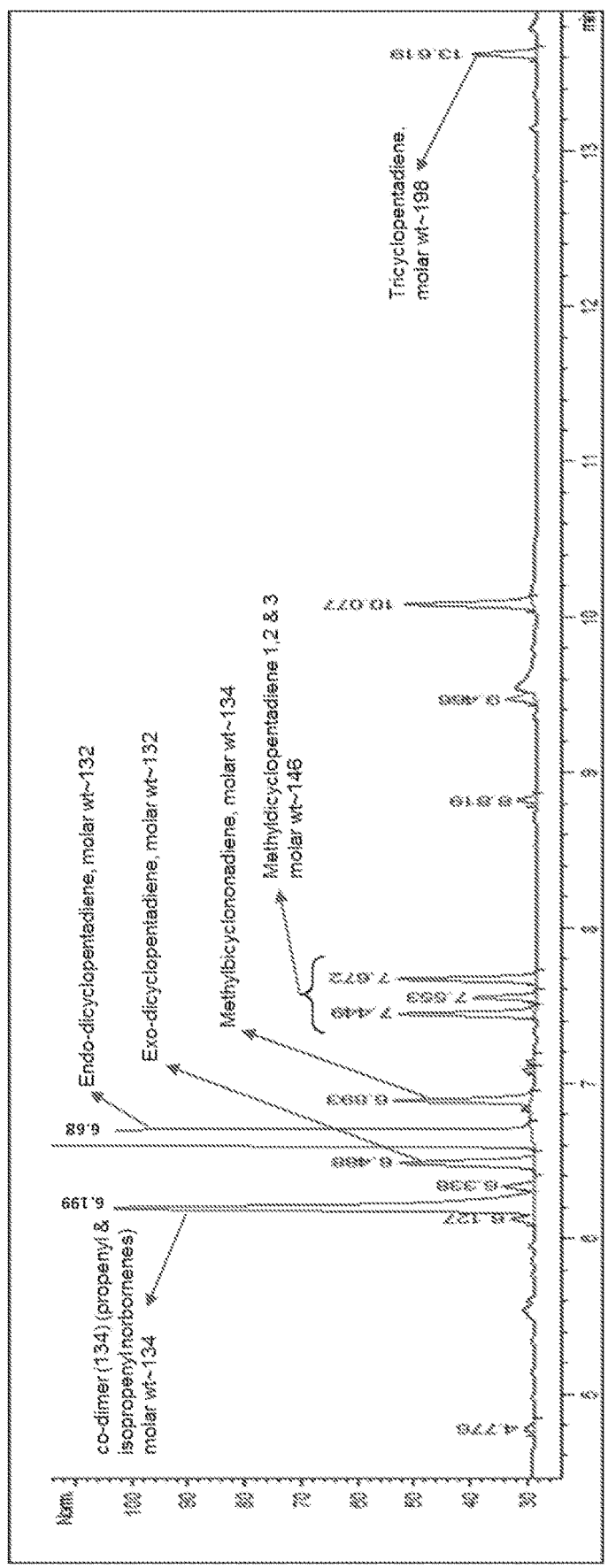
FIG. 6 represents a gas chromatogram of the mixed liquid hydrocarbon stream, obtained via a GC-FID.

The peaks in FIG. 6 were identified via a GC-MS technique [J. Chromatogr. Sci. (1971) 9 (10): 635-638]. Accordingly, the co-dimer (134), which includes propenyl and isopropenyl norbornene, was found to be eluted at around 6.2 min (as shown in FIG. 6). Therefore, the molar weight of the co-dimer was estimated to be around 134.11 g/mol.

Figure 7A:
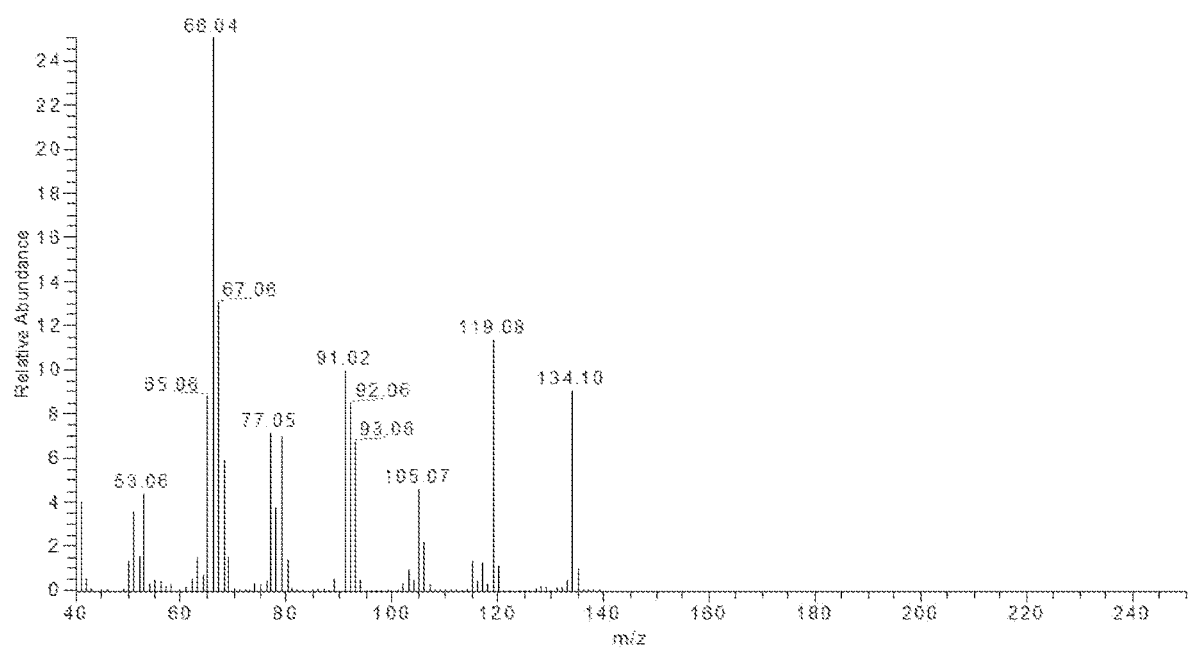
FIG. 7A represents a mass spectrum of a co-dimer (134) including propenyl and isopropenyl norbornene.
Figure 7B:
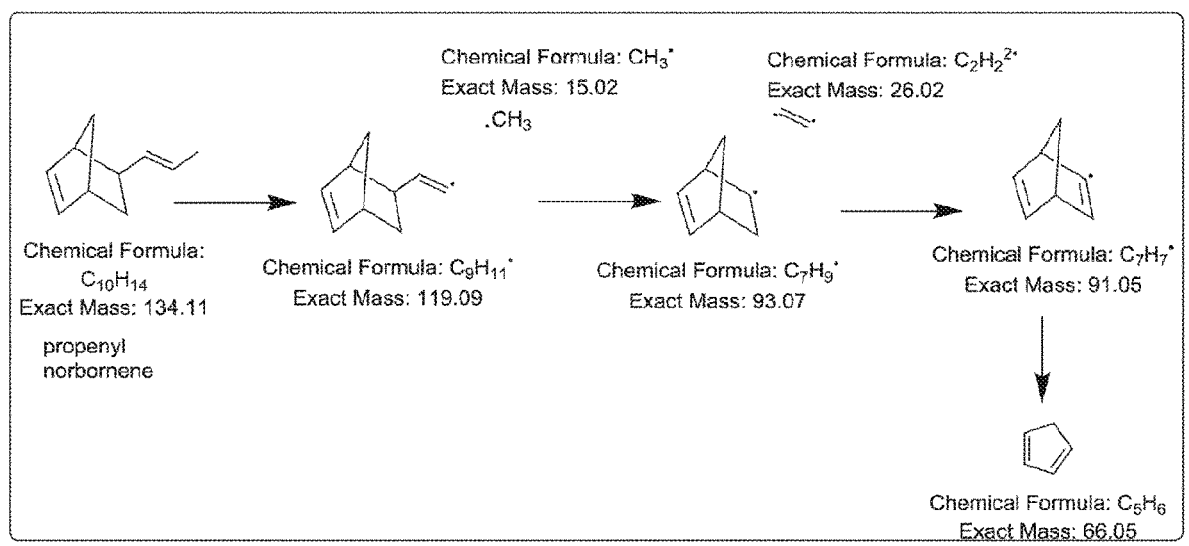
FIG. 7B represents a fragmentation pathway of a propenyl norbornene.
Figure 7C:
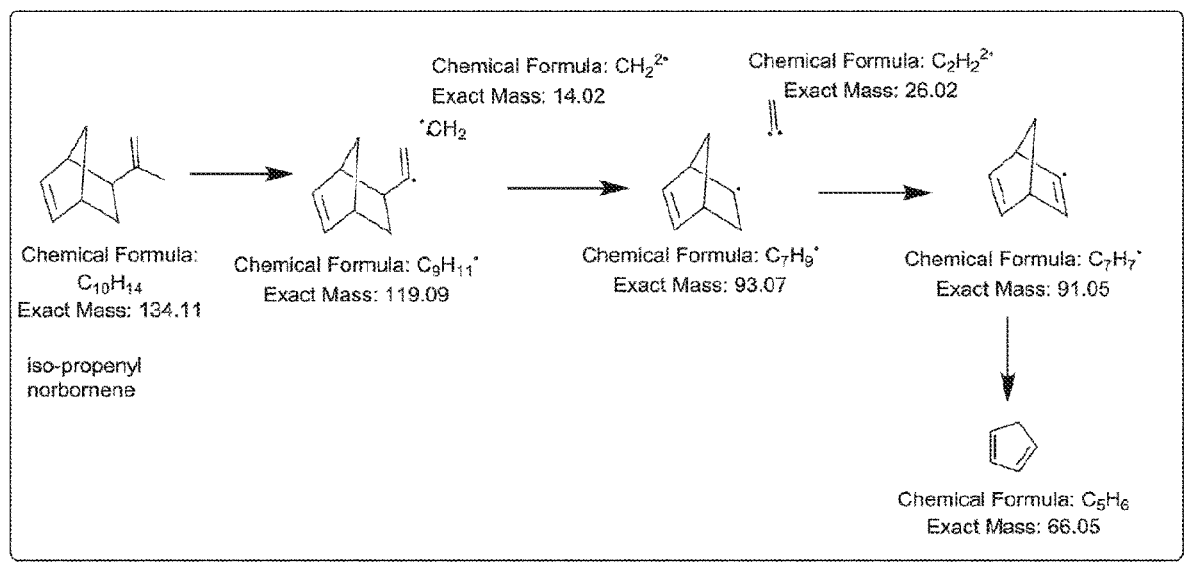
FIG. 7C represents a fragmentation pathway of an isopropenyl norbornene.

Furthermore, the mass spectrum of the co-dimer (134) was evaluated as shown in FIG. 7A. The structure of each of the propenyl and the isopropenyl norbornene was confirmed by the mass spectrum (as shown in FIG. 7A). As a result, the fragmentation pathway of each of the propenyl and the isopropenyl norbornene has been shown in FIGS. 7B and 7C, respectively. Accordingly, species having a molar weight of around 134.11 g/mol appear to be fragmented to species having molar weights of about 119, 93, 91, and 66 g/mol.

Example 10

Similarly, exo-dicyclopentadiene was found to be eluted at around 6.49 min (as shown in FIG. 6). Therefore, the molar weight of the exo-dicyclopentadiene was estimated to be around 132.09 g/mol.

Figure 8A:
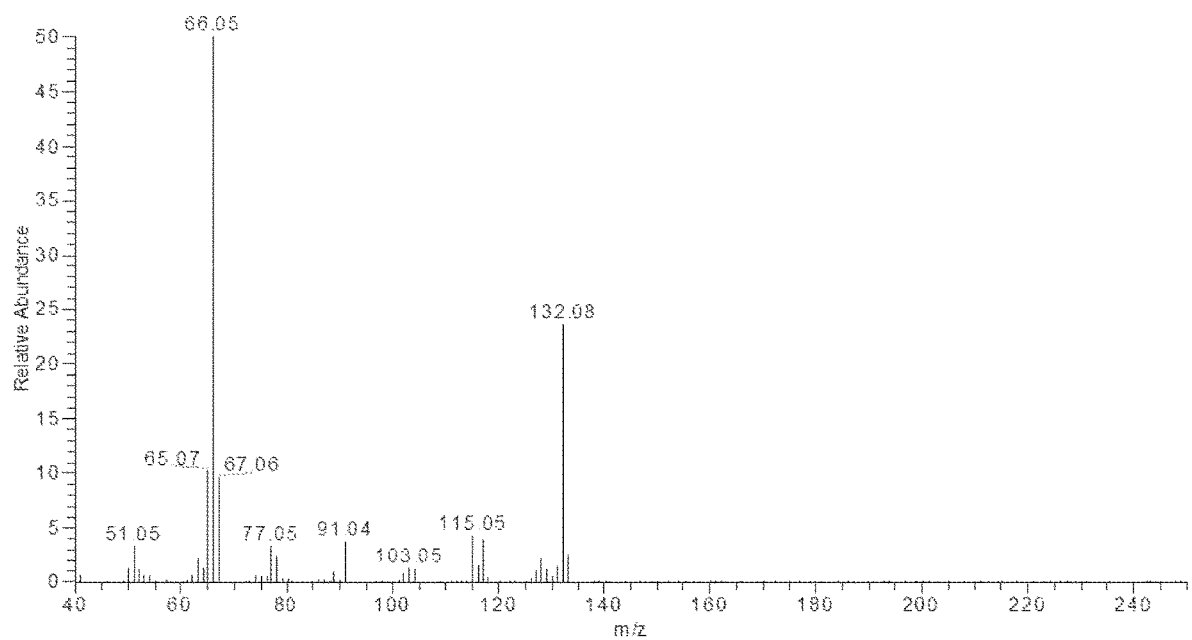
FIG. 8A represents a mass spectrum of an exo-dicyclopentadiene.
Figure 8B:
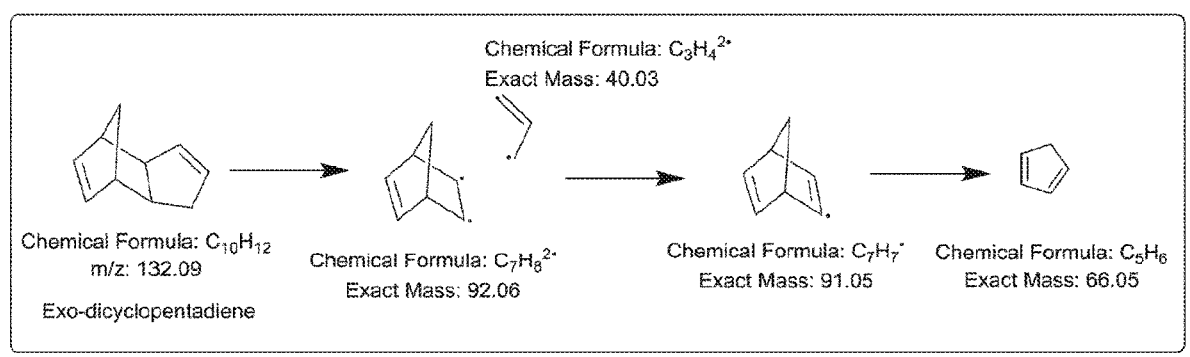
FIG. 8B represents a fragmentation pathway of an exo-dicyclopentadiene.

Furthermore, the mass spectrum of the exo-dicyclopentadiene was evaluated as shown in FIG. 8A. The structure of the exo-dicyclopentadiene was confirmed by the mass spectrum (as shown in FIG. 8A). As a result, the fragmentation pathway of the exo-dicyclopentadiene has been shown in FIG. 8B. Accordingly, species having a molar weight of around 132.09 g/mol appear to be fragmented to species having molar weights of about 91 and 66 g/mol.

Example 11

Likewise, endo-dicyclopentadiene was found to be eluted at around 6.68 min (as shown in FIG. 6). Therefore, the molar weight of the endo-dicyclopentadiene was estimated to be around 132.09 g/mol.

Figure 9A:
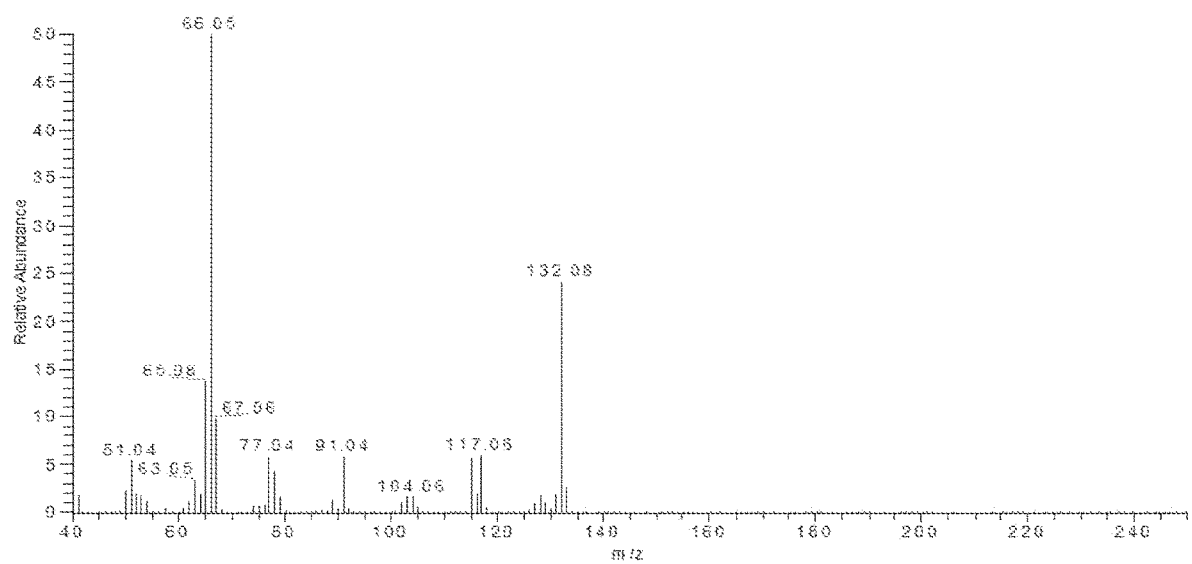
FIG. 9A represents a mass spectrum of an endo-dicyclopentadiene.
Figure 9B:
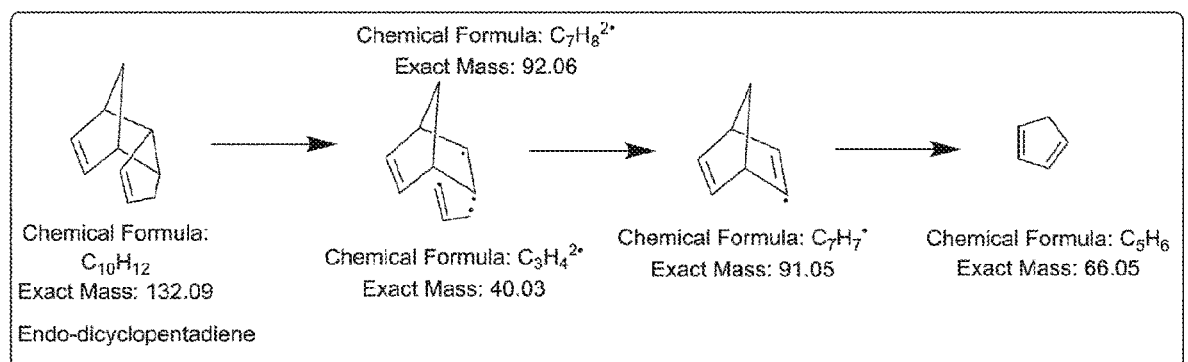
FIG. 9B represents a fragmentation pathway of an endo-dicyclopentadiene.

Furthermore, the mass spectrum of the endo-dicyclopentadiene was evaluated as shown in FIG. 9A. The structure of the endo-dicyclopentadiene was confirmed by the mass spectrum (as shown in FIG. 9A). As a result, the fragmentation pathway of the endo-dicyclopentadiene has been shown in FIG. 9B. Accordingly, species having a molar weight of around 132.09 g/mol appear to be fragmented to species having molar weights of about 91 and 66 g/mol.

Example 12

In addition, methylbicyclononadiene was found to be eluted at around 6.89 min (as shown in FIG. 6). Therefore, the molar weight of the methylbicyclononadiene was estimated to be around 134.11 g/mol.

Figure 10A:
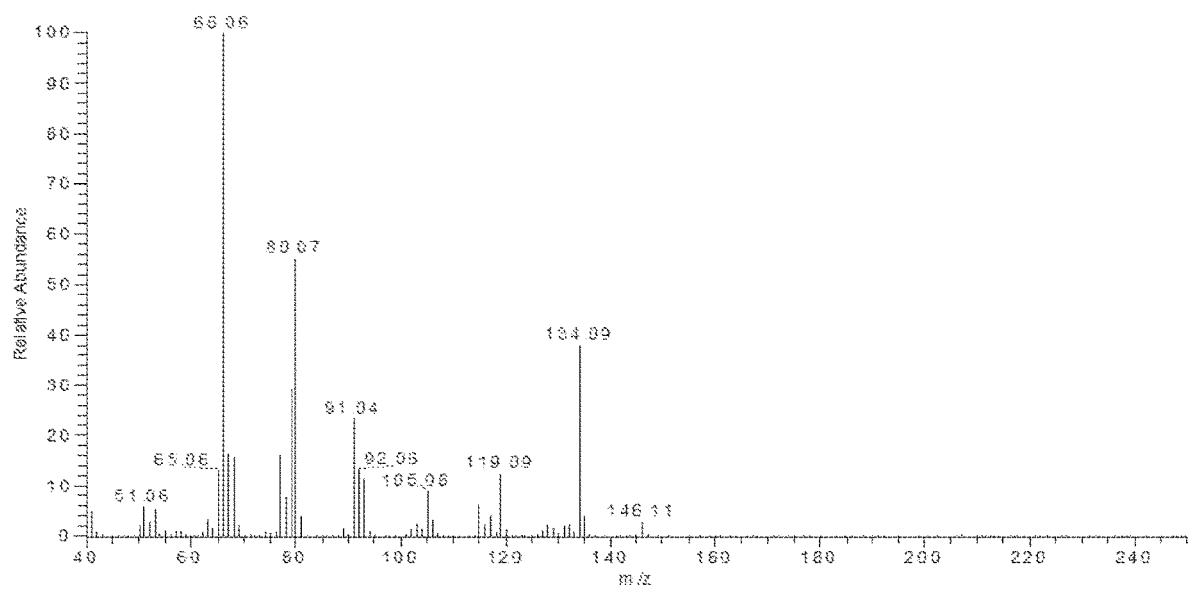
FIG. 10A represents a mass spectrum of a methylbicyclononadiene.
Figure 10B:
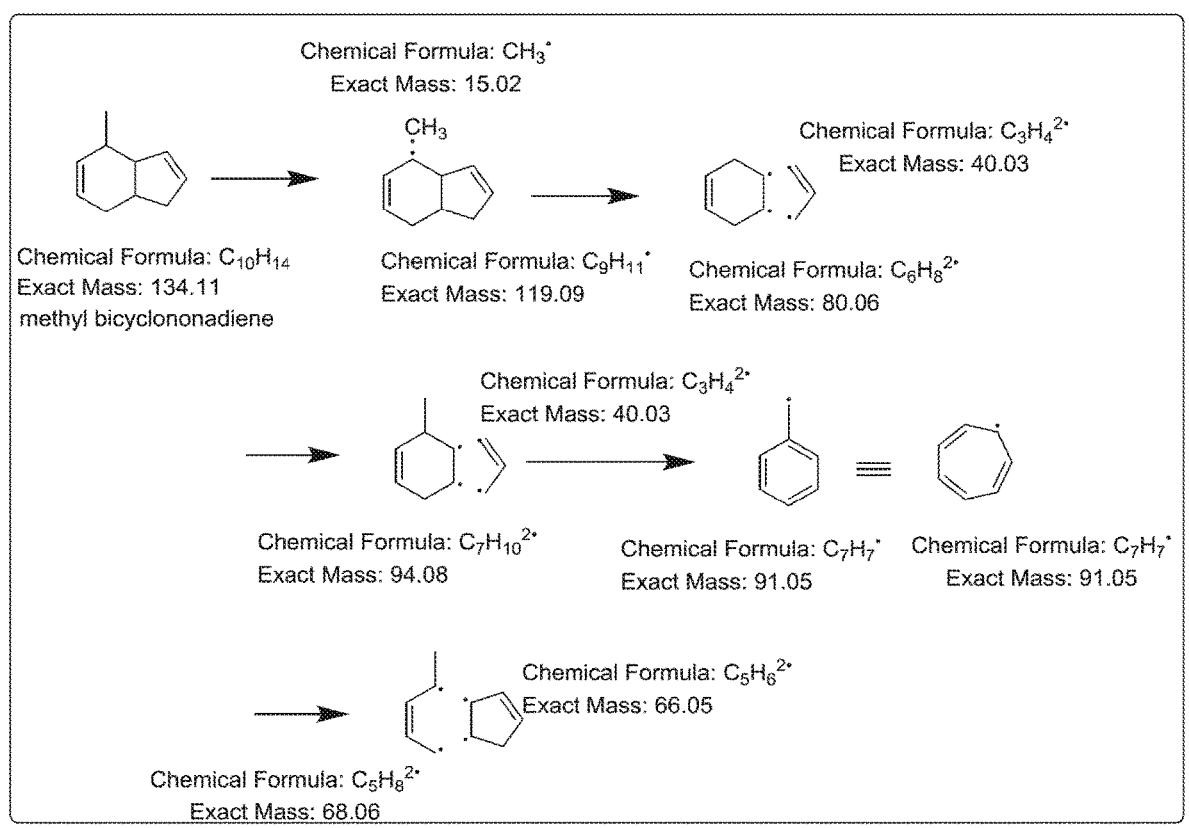
FIG. 10B represents a fragmentation pathway of a methylbicyclononadiene.

Furthermore, the mass spectrum of the methylbicyclononadiene was evaluated as shown in FIG. 10A. The structure of the methylbicyclononadiene was confirmed by the mass spectrum (as shown in FIG. 10A). As a result, the fragmentation pathway of the methylbicyclononadiene has been shown in FIG. 10B. Accordingly, species having a molar weight of around 134.11 g/mol appear to be fragmented to species having molar weights of about 119, 91, 80, and 66 g/mol.

Example 13

Similarly, methyldicyclopentadiene, which includes three different isomers of methyldicyclopentadiene, was found to be eluted at three elusion times i.e. around 7.45, 7.55, and 7.67 min, respectively (as shown in FIG. 6). Therefore, an average molar weight of the methyldicyclopentadiene was estimated to be around 146.11 g/mol.

Figure 11A:
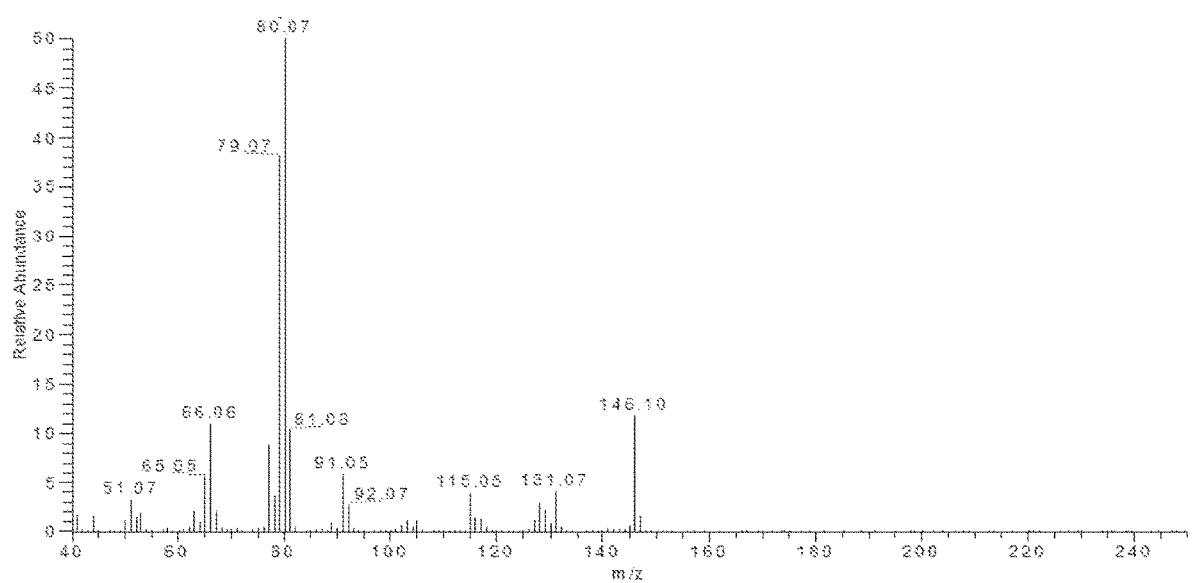
FIG. 11A represents a mass spectrum of a methyldicyclopentadiene.
Figure 11B:
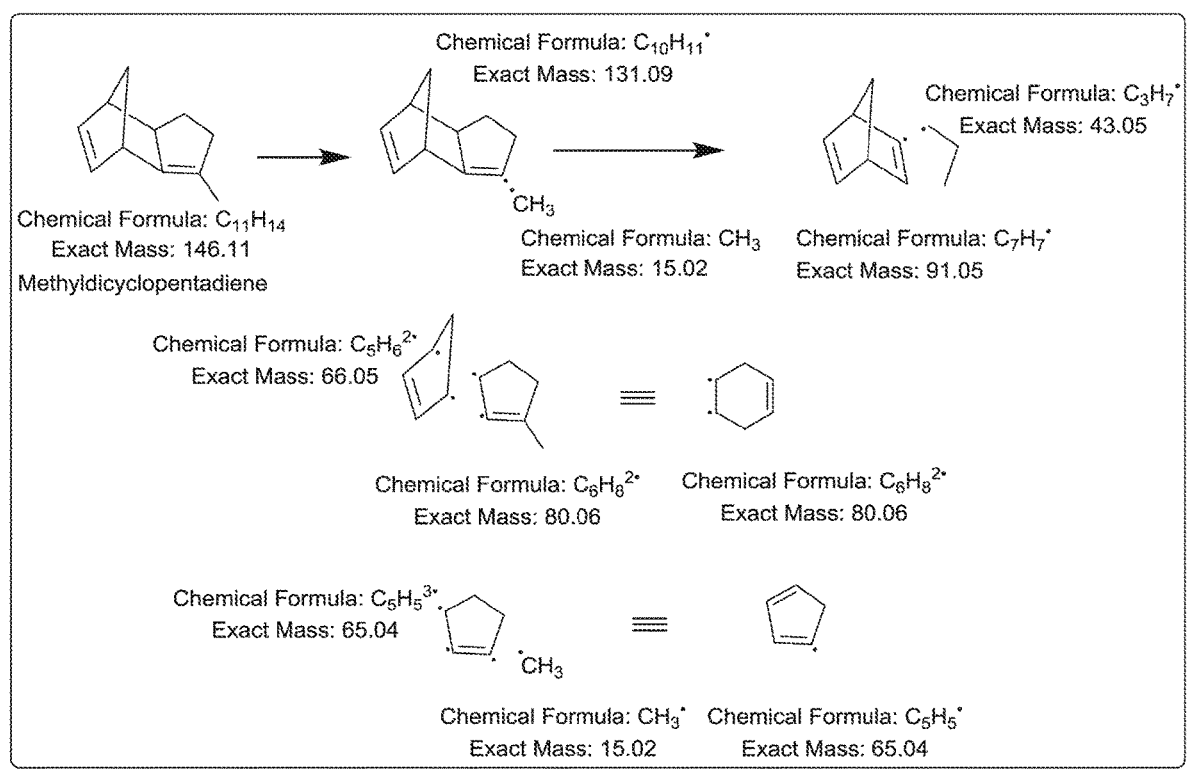
FIG. 11B represents a fragmentation pathway of a methyldicyclopentadiene.

Furthermore, the mass spectrum of the methyldicyclopentadiene was evaluated as shown in FIG. 11A. The structure of the methyldicyclopentadiene was confirmed by the mass spectrum (as shown in FIG. 11A). As a result, the fragmentation pathway of the methyldicyclopentadiene has been shown in FIG. 11B. Accordingly, species having a molar weight of around 146.11 g/mol appear to be fragmented to species having molar weights of about 131, 91, 80, 66, and 65 g/mol.

Example 14

Tricyclopentadiene was found to be eluted at three elusion times i.e. around 13.62 min (as shown in FIG. 6). Therefore, an average molar weight of the tricyclopentadiene was estimated to be around 198.14 g/mol.

Figure 12A:
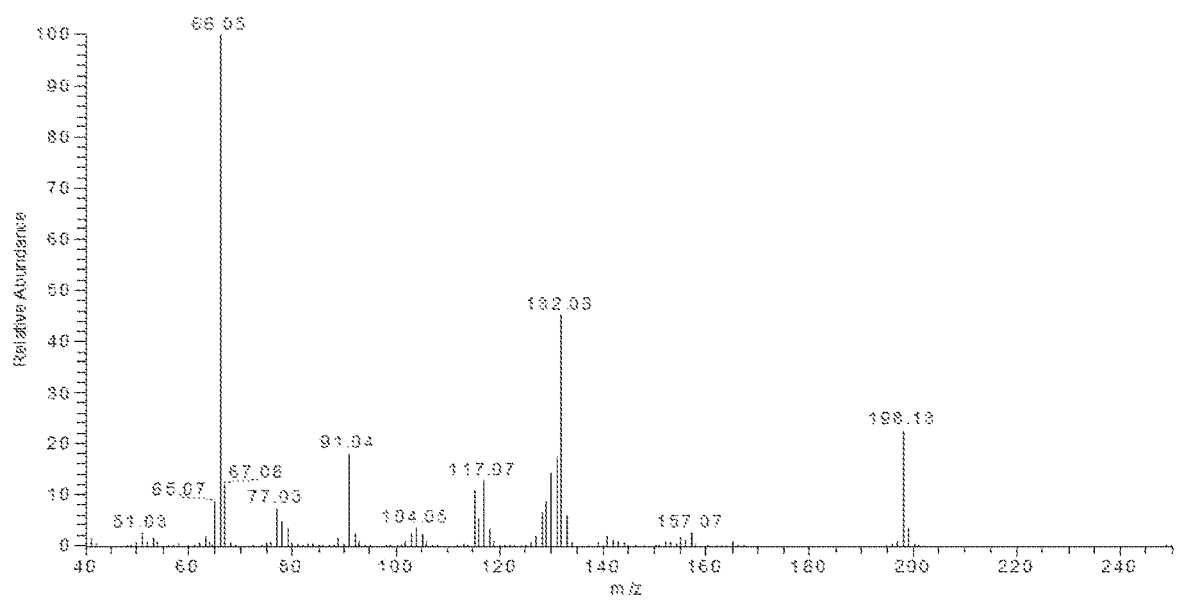
FIG. 12A represents a mass spectrum of a tricyclopentadiene.
Figure 12B:
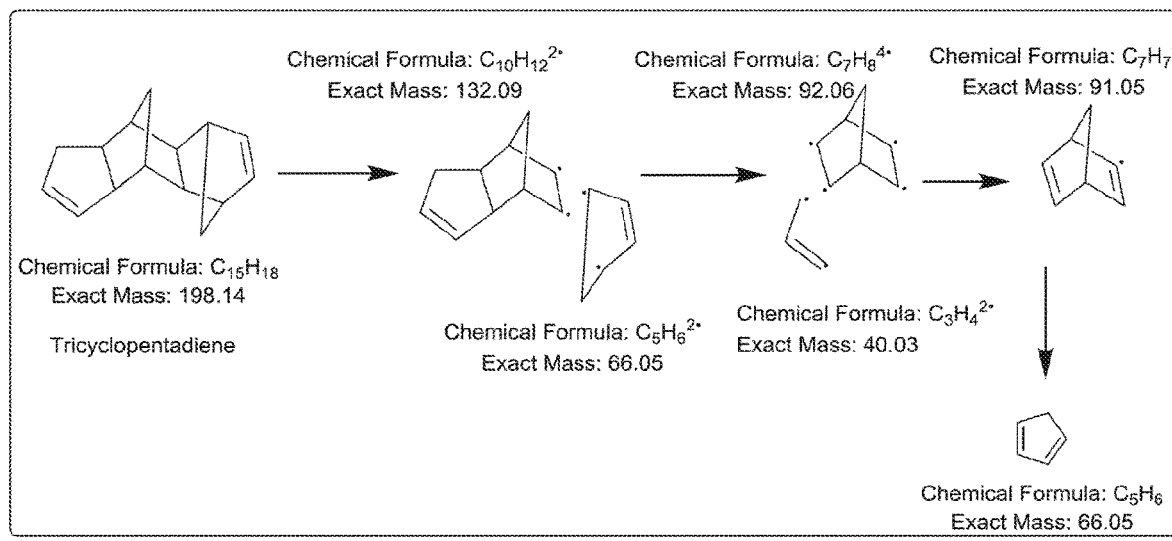
FIG. 12B represents a fragmentation pathway of a tricyclopentadiene.

Furthermore, the mass spectrum of the tricyclopentadiene was evaluated as shown in FIG. 12A. The structure of the tricyclopentadiene was confirmed by the mass spectrum (as shown in FIG. 12A). As a result, the fragmentation pathway of the tricyclopentadiene has been shown in FIG. 12B. Accordingly, species having a molar weight of around 198.14 g/mol appear to be fragmented to species having molar weights of about 132, 91, and 66 g/mol.

The invention claimed is:

1. A dynamic method for purifying dicyclopentadiene from a mixed liquid hydrocarbon stream, comprising:
    delivering at least a portion of the mixed liquid hydrocarbon stream to an inlet port of a separation/purification unit, wherein the mixed liquid hydrocarbon stream comprises dicyclopentadiene and one or more of a $C_5$ paraffin, a $C_5$ olefin, co-dimers, cyclopentadiene, benzene, vinyl norbornene, bicyclononadiene, propenyl norbornene, isopropenyl norbornene, methylbicyclononadiene, and methyldicyclopentadiene;
    dividing the mixed liquid hydrocarbon stream to form a plurality of mixed liquid hydrocarbon streams and flowing the plurality of mixed liquid hydrocarbon streams through a low temperature region of the separation/purification unit;
    continuously contacting the plurality of mixed liquid hydrocarbon streams with an inner wall of the separation/purification unit to form an impure crystalline slurry comprising an impure crystalline phase, and an excess liquid phase, wherein dicyclopentadiene crystals are present in the impure crystalline phase;
    depositing the impure crystalline phase on the inner wall of the separation/purification unit;
    recycling at least a portion of the excess liquid phase to the inlet port of the separation/purification unit;
    sweating the impure crystalline phase at least once to a sweating temperature to at least partially melt the impure crystalline phase to form a purified crystalline phase comprising the dicyclopentadiene crystals and a molten impurity phase and separating the molten impurity phase from the purified crystalline phase;
    melting the dicyclopentadiene crystals on the inner wall of the separation/purification unit to form molten dicyclopentadiene and collecting the molten dicyclopentadiene.

2. The dynamic method of claim 1, further comprising delivering the molten dicyclopentadiene to a second separation/purification unit located downstream of the separation/purification unit to produce the molten dicyclopentadiene having purity of at least 90%.

3. The dynamic method of claim 1, wherein the impure crystalline phase is sweated once to form the purified crystalline phase and the molten impurity phase.

4. The dynamic method of claim 1, wherein the impure crystalline phase is sweated more than once to form the purified crystalline phase and the molten impurity phase, wherein the sweating temperature is increased for each sweating operation relative to a previous sweating temperature.

5. The dynamic method of claim 4, which produces the molten dicyclopentadiene having a purity that is higher than a substantially similar process where the impure crystalline phase is sweated once.

6. The dynamic method of claim 1, further comprising removing impurities to supersaturate the mixed liquid hydrocarbon stream prior to the delivering.

7. The dynamic method of claim 1, wherein the mixed liquid hydrocarbon stream comprises 75% to 94% dicyclopentadiene by weight prior to the delivering.

8. The dynamic method of claim 1, wherein the excess liquid phase comprises an impure fraction and the method further comprises purging the impure fraction from the excess liquid phase prior to the recycling to form a purged impure fraction.

9. The dynamic method of claim 8, further comprising fractionally distilling the purged impure fraction with a distillation column to recover a residual dicyclopentadiene.

10. The dynamic method of claim 9, further comprising combining the residual dicyclopentadiene with the molten dicyclopentadiene to give a final yield of dicyclopentadiene that is higher than a method without combining.

11. The dynamic method of claim 1, further comprising purifying the molten impurity phase with an auxiliary separation/purification unit to recover molten dicyclopentadiene from the molten impurity phase.

12. The dynamic method of claim 11, further comprising combining the molten dicyclopentadiene from the auxiliary separation/purification unit with the molten dicyclopentadiene from the separation/purification unit to give a final yield of dicyclopentadiene that is higher than a method without combining.

13. The dynamic method of claim 1, further comprising collecting the excess liquid phase in a reservoir located downstream of the separation/purification unit and recycling at least a portion of the excess liquid phase from the reservoir to the inlet of the separation/purification unit.

14. The dynamic method of claim 1, which is performed in a temperature range of 0 to 40° C.

15. A cascade process for purifying dicyclopentadiene from a mixed liquid hydrocarbon stream, comprising:
   delivering at least a portion of the mixed liquid hydrocarbon stream to an inlet port of a first separation/purification unit, wherein the mixed liquid hydrocarbon stream comprises dicyclopentadiene and one or more of a $C_5$ paraffin, a $C_5$ olefin, co-dimers, cyclopentadiene, benzene, vinyl norbornene, bicyclononadiene, propenyl norbornene, isopropenyl norbornene, methylbicyclononadiene, and methyldicyclopentadiene;
   dividing the mixed liquid hydrocarbon stream to form a plurality of mixed liquid hydrocarbon streams and flowing the plurality of mixed liquid hydrocarbon streams through a low temperature region of the first separation/purification unit;
   continuously contacting the plurality of mixed liquid hydrocarbon streams with an inner wall of the first separation/purification unit to form an impure crystalline slurry comprising an impure crystalline phase, and an excess liquid phase, wherein dicyclopentadiene crystals are present in the impure crystalline phase;
   depositing the impure crystalline phase on the inner wall of the first separation/purification unit;
   recycling at least a portion of the excess liquid phase to the inlet port of the first separation/purification unit;
   sweating the impure crystalline phase at least once to a sweating temperature to at least partially melt the impure crystalline phase to form a purified crystalline phase comprising the dicyclopentadiene crystals and a molten impurity phase and separating the molten impurity phase from the purified crystalline phase;
   melting the dicyclopentadiene crystals on the inner wall of the first separation/purification unit to form a first molten dicyclopentadiene;
   delivering the first molten dicyclopentadiene to a second separation/purification unit located downstream of the first separation/purification unit and repeating the dividing, the continuously contacting, the depositing, the recycling, the sweating, and the melting in the second separation/purification unit to form a second molten dicyclopentadiene that has a higher purity than the first molten dicyclopentadiene.

* * * * *